US012226296B2

(12) United States Patent
Borgmann et al.

(10) Patent No.: US 12,226,296 B2
(45) Date of Patent: Feb. 18, 2025

(54) METHOD FOR PRODUCING ABSORBENT ARTICLES COMPRISING WATER-ABSORBING RESIN

(71) Applicant: The Procter & Gamble Company, Cincinnati, OH (US)

(72) Inventors: Carolin Michaela Borgmann, Eschborn (DE); Heike Opper, Bad Soden (DE); Arsen Arsenov Simonyan, Koenigstein (DE); Yoshiro Mitsukami, Himeji (JP); Keisuke Kikuchi, Himeji (JP)

(73) Assignee: The Procter & Gamble Company, Cincinnati, OH (US)

( * ) Notice: Subject to any disclaimer, the term of this patent is extended or adjusted under 35 U.S.C. 154(b) by 517 days.

(21) Appl. No.: 17/698,069

(22) Filed: Mar. 18, 2022

(65) Prior Publication Data

US 2022/0296438 A1 Sep. 22, 2022

(30) Foreign Application Priority Data

Mar. 18, 2021 (JP) ................................ 2021-045197
Dec. 20, 2021 (JP) ................................ 2021-206110

(51) Int. Cl.

| | |
|---|---|
| ***A61F 13/53*** | (2006.01) |
| ***A61F 13/00*** | (2024.01) |
| ***C08F 2/10*** | (2006.01) |
| ***C08F 6/06*** | (2006.01) |
| ***C08F 20/06*** | (2006.01) |
| ***C08J 3/24*** | (2006.01) |
| *A61F 13/15* | (2006.01) |

(52) U.S. Cl.

CPC ................ *A61F 13/53* (2013.01); *C08F 2/10* (2013.01); *C08F 6/06* (2013.01); *C08F 20/06* (2013.01); *C08J 3/245* (2013.01); *A61F 2013/15463* (2013.01); *A61F 2013/530591* (2013.01); *A61F 2013/530729* (2013.01); *A61F 2013/530737* (2013.01)

(58) Field of Classification Search

CPC .... A61F 13/53; C08F 2/10; C08F 6/06; C08F 20/06; C08J 3/245

See application file for complete search history.

(56) References Cited

U.S. PATENT DOCUMENTS 3,001,565 A * 9/1961 Beach .................. A61G 7/0503 383/7
4,914,170 A * 4/1990 Chang .................. C08F 220/06 526/240
8,912,298 B2 * 12/2014 Matsumoto ............. C07C 51/50 526/240
9,982,110 B2 * 5/2018 Hosomi .................. C07C 41/03
11,224,857 B2 * 1/2022 Tamaki ................ B01J 20/3085
11,459,431 B2 * 10/2022 Wada ...................... A61L 15/42
2006/0183828 A1 * 8/2006 Dairoku ............... B01J 20/3028 524/419
2007/0238806 A1 * 10/2007 Mitsukami ............. A61L 15/60 522/150
2009/0318885 A1 * 12/2009 Dairoku .................. A61L 15/24 502/402
2010/0072421 A1 * 3/2010 Kitano .................... A61L 15/24 525/330.3
2010/0120940 A1 * 5/2010 Adachi ..................... C08F 2/10 523/111
2010/0240823 A1 * 9/2010 Sakamoto ............... A61L 15/60 524/543
2010/0261850 A1 * 10/2010 Mitsukami ............... C08J 3/245 524/832
2012/0045639 A1 * 2/2012 Whitmore ............... A61F 13/15 428/327
2012/0258851 A1 * 10/2012 Nakatsuru ................. C08J 3/12 502/7
2013/0026412 A1 * 1/2013 Machida ............... C08F 220/06 525/384
2013/0066019 A1 * 3/2013 Okuda ....................... C08J 3/24 525/329.7
2014/0031473 A1 * 1/2014 Nogi ....................... C08F 20/06 525/383
2014/0193641 A1 * 7/2014 Torii ....................... A61L 15/26 252/194

(Continued)

FOREIGN PATENT DOCUMENTS

JP 2021045197 A 3/2021

OTHER PUBLICATIONS

PCT Search Report and Written Opinion for PCT/US2022/020852 dated Jul. 4, 2022, 16 pages.

*Primary Examiner* — Guy K Townsend
(74) *Attorney, Agent, or Firm* — William E. Gallagher; Sarah M. Decristofaro

(57) ABSTRACT

Provided is a method for producing an absorbent article comprising a water-absorbing resin having an excellent initial water absorption speed under load even substantially without adding a liquid permeability enhancer.

The method steps for producing the water-absorbing resin includes the step of polymerizing a monomer while adding certain polyalkylene glycol thereto so as to generate, during or after the polymerization, a crosslinked hydrogel polymer containing the polyalkylene glycol of a specific molecular weight, wherein the crosslinked hydrogel polymer has a centrifuge retention capacity within a given range and a final water-absorbing resin to be obtained has various physical properties (CRC, AAP, SFC, FSR) being within given ranges.

12 Claims, No Drawings

(56) References Cited

U.S. PATENT DOCUMENTS

| | | | | |
|---|---|---|---|---|
| 2015/0011388 | A1* | 1/2015 | Matsumoto | A61L 15/60 521/149 |
| 2015/0210843 | A1* | 7/2015 | Kimura | B01J 20/267 525/187 |
| 2015/0217270 | A1* | 8/2015 | Ueda | B01J 20/28011 502/402 |
| 2015/0225514 | A1* | 8/2015 | Kimura | A61L 15/24 525/344 |
| 2015/0367018 | A1* | 12/2015 | Oshima | A61L 15/60 525/329.9 |
| 2017/0281422 | A1* | 10/2017 | Herfert | A61F 13/534 |
| 2017/0281423 | A1* | 10/2017 | Panayotova | A61F 13/53 |
| 2017/0281425 | A1* | 10/2017 | Herfert | A61F 13/535 |
| 2017/0312148 | A1* | 11/2017 | Dobrosielska-Oura | A61F 13/539 |
| 2018/0071714 | A1* | 3/2018 | Torii | B01J 20/261 |
| 2018/0298132 | A1* | 10/2018 | Yorino | C08F 220/00 |
| 2018/0303968 | A1* | 10/2018 | Simonyan | C08K 3/346 |
| 2018/0304233 | A1* | 10/2018 | Simonyan | C08J 3/245 |
| 2018/0305519 | A1* | 10/2018 | Kamphus | C08K 7/00 |
| 2019/0070586 | A1* | 3/2019 | Jiang | B01J 20/267 |
| 2020/0121521 | A1* | 4/2020 | Daniel | A61F 13/53 |
| 2021/0008521 | A1* | 1/2021 | Choi | B01J 20/28028 |
| 2021/0268139 | A1* | 9/2021 | Yang | C08J 3/245 |

* cited by examiner

METHOD FOR PRODUCING ABSORBENT ARTICLES COMPRISING WATER-ABSORBING RESIN

TECHNICAL FIELD

The present invention relates to a method for producing an absorbent article comprising water-absorbing resin.

BACKGROUND

A super absorbent polymer (SAP) is used as an absorbent core included in absorbent articles such as paper diapers, sanitary napkins, and so-called incontinence pads. Generally used as the SAP is a surface-crosslinked water-absorbing resin.

As used in any of the above-described absorbent articles, a water-absorbing resin absorbs an aqueous liquid such as urine and is swollen thereby, so that the water-absorbing resin keeps the aqueous liquid in its inside. Thus, the water-absorbing resin needs to have a high absorption capacity of the aqueous liquid, and is also required to have a high water absorption speed, since the water-absorbing resin needs to quickly absorb the aqueous liquid. As a physical property value expressing the water absorption speed of the water-absorbing resin, a free swell rate (FSR) may be employed.

In addition to the high absorption capacity and the high water absorption speed, the water-absorbing resin is required to have a favorable liquid permeability. With a water-absorbing resin having a low liquid permeability, a discharged liquid may not go inside an absorbent article and may remain in or at a location close to the surface. This may possibly lead to leakage of the liquid from the absorbent article. As a physical property value expressing the liquid permeability, a saline flow conductivity (SFC) may be employed.

Patent Literatures 7 to 12 disclose a water-absorbing resin having an improved T20 (i.e., time to reach an uptake of 20 g/g), which is used as a parameter indicative of an initial water absorption speed under load. As a method for improving the T20 in the water-absorbing resin, Patent Literature 8 describes foaming polymerization, and Patent Literatures 9 to 12 describe gel-crushing under specific crushing conditions.

As a technique for improving the FSR in the water-absorbing resin, Patent Literatures 14 and 15 disclose a so-called wet grinding technique that uses a gel-crusher with a small die diameter to apply a strong shearing force to a gel when crushing the gel.

Patent Literature 1 discloses a technique according to which a substance (e.g., a surfactant) for suppressing adhesion between gel particles is added during polymerization of a water-absorbing resin or during gel-crushing, for the purpose of reducing adhesion between crushed gel particles. Patent Literature 4 discloses use of polyethylene glycol (PEG) as a releasing agent during gel-crushing.

Patent Literature 3 discloses a water-absorbing resin containing a compound derived from polyalkylene glycol and a polyvalent metal salt. Patent Literature 5 discloses adding a water-soluble polymer to a water-absorbing resin in order to increase the water absorption speed. Patent Literature 2 discloses adding PEG to a water-absorbing resin to suppress initial coloration of the water-absorbing resin. Patent Literature 6 discloses that a polyhydric alcohol such as PEG is solely used as an internal crosslinking agent. Patent Literature 13 discloses that PEG is used as a thickener in foaming polymerization.

CITATION LIST

Patent Literature

[Patent Literature 1]
Pamphlet of International Publication No. 2016/204302
[Patent Literature 2]
Pamphlet of International Publication No. 2008/096713
[Patent Literature 3]
Pamphlet of International Publication No. 2009/075204
[Patent Literature 4]
Japanese Patent Application Publication Tokukai No. 2001-342258
[Patent Literature 5]
Japanese Patent Application Publication, Tokukaishou, No. 57-167307 (1982)
[Patent Literature 6]
Japanese Patent Application Publication, Tokukaishou, No. 55-84304 (1980)
[Patent Literature 7]
Published Japanese Translation of PCT International Application, Tokuhyo, No. 2014-515987
[Patent Literature 8]
Pamphlet of International Publication No. 2010/095427
[Patent Literature 9]
Pamphlet of International Publication No. 2017/164452
[Patent Literature 10]
Pamphlet of International Publication No. 2018/117391
[Patent Literature 11]
Pamphlet of International Publication No. 2018/139768
[Patent Literature 12]
Pamphlet of International Publication No. 2016/085123
[Patent Literature 13]
Pamphlet of International Publication No. 2016/204390
[Patent Literature 14]
Pamphlet of International Publication No. 2016/126079
[Patent Literature 15]
Pamphlet of International Publication No. 2016/158975

SUMMARY OF INVENTION

Technical Problem

Absorbent articles such as paper diapers including the above-described known water-absorbing resins are still relatively slow to absorb an aqueous liquid and permit exuding (re-wet) of the aqueous liquid, disadvantageously. In an approach to overcome these disadvantages in terms of the water-absorbing resin, the inventors of the present invention found it important to improve the initial water absorption speed under load. That is, the water-absorbing resin is required to be capable of quickly diffusing and absorbing an aqueous liquid at an initial phase of contact between an absorbent article including the water-absorbing resin and the aqueous liquid.

Incidentally, in a case where a liquid permeability enhancer is added to a water-absorbing resin, a problem involving dust may occur. For example, dusting and/or filter clogging may occur during production of a water-absorbing resin and in a production line of paper diapers. In light of this, it is necessary to improve the initial water absorption speed under load substantially without adding the liquid permeability enhancer to the water-absorbing resin.

An aspect of the present invention has an object to provide a method for producing an absorbent article comprising a water-absorbing resin that has an excellent initial water absorption speed under load even substantially without adding a liquid permeability enhancer.

Solution to Problem

In order to attain the object, a method in accordance with an aspect of the present invention for producing an absorbent article comprising a water-absorbing resin is as follows.

In the method for producing an absorbent article, comprising a surface-crosslinked particulate poly(meth)acrylic acid (salt)-based water-absorbing resin, the method includes the steps of:

(i) preparing a (meth)acrylic acid (salt)-based aqueous monomer solution;

(ii) polymerizing the (meth)acrylic acid (salt)-based aqueous monomer solution;

(iii) carrying out gel-crushing of a crosslinked hydrogel polymer generated during or after the polymerization to obtain a particulate hydrogel;

(iv) drying the particulate hydrogel to obtain a dried polymer;

(v) pulverizing and/or classifying the dried polymer to obtain a particulate water-absorbing resin before surface-crosslinking;

(vi) surface-crosslinking the particulate water-absorbing resin before surface-crosslinking; and (vii) incorporating the surface-crosslinked particulate water-absorbing resin in an absorbent article, wherein in the step (i) and/or the step (ii), water-soluble polyalkylene glycol having a weight average molecular weight of not more than 2000 is added to the aqueous monomer solution so that a total amount of the water-soluble polyalkylene glycol added in the step (i) and/or the step (ii) is 0.01 mass % to 1 mass % relative to a total mass of a monomer included in the aqueous monomer solution, the crosslinked hydrogel polymer has a centrifuge retention capacity of not more than 31 g/g and not less than 20 g/g, and the surface-crosslinked particulate poly(meth)acrylic acid (salt)-based water-absorbing resin obtained by said method satisfies (1) to (4) below:

(1) a centrifuge retention capacity (CRC) of not less than 20 g/g and not more than 35 g/g;

(2) an absorption against pressure (AAP), measured under a load of 0.7 psi, of not less than 25 g/g;

(3) a saline flow conductivity (SFC) of not less than 15 (×10-7 cm3·sec/g); and (4) a free swell rate (FSR) of not less than 0.33 g/(g s).

Preferably, in the method in accordance with the aspect of the present invention, the polyalkylene glycol has a weight average molecular weight of not less than 200.

Preferably, in the method in accordance with the aspect of the present invention, a content of the polyalkylene glycol is adjusted to 0.01 mass % to 1 mass % relative to the entire surface-crosslinked particulate poly(meth)acrylic acid (salt)-based water-absorbing resin.

Preferably, in the method in accordance with the aspect of the present invention, the surface-crosslinked particulate poly(meth)acrylic acid (salt)-based water-absorbing resin to be incorporated into an absorbent article is a surface-crosslinked water-absorbing resin having a non-uniformly pulverized shape.

Preferably, in the method in accordance with the aspect of the present invention, the surface-crosslinked particulate poly(meth)acrylic acid (salt)-based water-absorbing resin to be incorporated into an absorbent article has a moisture content of not more than 5 mass %.

Preferably, in the method in accordance with the aspect of the present invention, the particulate hydrogel obtained as a result of the gel-crushing of the crosslinked hydrogel polymer in the step (iii) has a logarithmic standard deviation (σ) of 0.2 to 1.5, the logarithmic standard deviation (σ) indicating a particle size distribution of the particulate hydrogel.

Advantageous Effects of Invention

A method in accordance with an aspect of the present invention for producing an absorbent article comprising a water-absorbing resin provides a water-absorbing resin having an excellent initial water absorption speed under load (T20) even substantially without adding a liquid permeability enhancer. Therefore, for example, in a case where an absorbent article, such as a paper diaper is produced to comprise a water-absorbing resin produced by the production method in accordance with the aspect of the present invention, the absorbent article can achieve an excellent liquid permeability through a swollen gel, can absorb an aqueous liquid quickly, and can suppress or reduce exuding (re-wet) of the aqueous liquid. Since the aspect of the present invention substantially does not include addition of the liquid permeability enhancer, it is possible to suppress or reduce problems involving dust, such as dusting and/or filter clogging that may otherwise occur during production of a water-absorbing resin and in a production line of paper diapers. Furthermore, it is possible to provide absorbent articles that are safer to consumers.

DESCRIPTION OF EMBODIMENTS

The following will provide a specific explanation of embodiments of the present invention. The present invention is not limited to the embodiments, but can be altered by a skilled person in the art within the descriptions. The present invention also encompasses, in its technical scope, any embodiment and any example derived by combining technical means disclosed in differing embodiments and examples. Herein, a range "A to B" means "not less than A and not more than B", unless otherwise specified. The term "(meth)acrylic" means "acrylic and/or methacrylic". A mass of a water-absorbing resin and the like is a value in terms of solid content, unless otherwise specified.

[1] Definition of Terms

(1-1) Water-Absorbing Resin

A "water-absorbing resin" herein means a crosslinked polymer having a water-swelling property and water-insolubility. The "water-swelling property" herein means an absorption capacity without load (also referred to as a centrifuge retention capacity (CRC)) of not less than 5 g/g defined according to NWSP 241.0.R2(15). The "water-insolubility" herein means a water-soluble content (Ext) of not more than 50 mass % defined according to NWSP 270.0.R2(15).

The "water-absorbing resin" is preferably a hydrophilic crosslinked polymer obtained by polymerizing and crosslinking a (meth)acrylic acid (salt) monomer. Note that the water-absorbing resin does not have to contain the hydrophilic crosslinked polymer in its total amount, i.e., in an amount of 100 mass %. The water-absorbing resin may contain an additive(s) and/or the like in an amount with which the required performance such as the CRC and the Ext can be satisfied.

The water-absorbing resin herein may refer to a "polymer that is crosslinked only in its internal part (i.e., a polymer having an internal part and a surface whose crosslinking densities are substantially equal to each other)" or a "polymer that is crosslinked in its internal part and in its surface (i.e., a polymer having a surface whose crosslinking density is relatively higher than a crosslinking density of an internal part of the polymer)". Herein, basically, the "polymer that is crosslinked only in its internal part" and the "polymer that is crosslinked in its internal part and in its surface" are not distinguished from each other, and each of them is described as a "water-absorbing resin". However, there may be a case where a polymer whose surface is crosslinked and a polymer whose surface is not crosslinked need to be distinguished from each other. In such a case, the "polymer that is crosslinked only in its internal part" is described as a "water-absorbing resin before surface-crosslinking" or a "base polymer", since the "polymer that is crosslinked only in its internal part" has not been subjected to surface-crosslinking yet. Meanwhile, the "polymer that is cross-linked in its internal part and in its surface (i.e., a polymer having a surface whose crosslinking density is relatively higher than a crosslinking density of an internal part of the polymer)" is described as a "water-absorbing resin after surface-crosslinking" or a "surface-crosslinked water-absorbing resin", since the "polymer that is crosslinked in its internal part and in its surface" has been subjected to surface-crosslinking. Note that the expression "before surface-crosslinking" means "before a surface-crosslinking agent is added" or "after a surface-crosslinking agent is added but before a surface-crosslinking reaction by a heating treatment is started".

The "water-absorbing resin" may refer to a resin containing only a resin component or a resin containing a resin component and other component(s) such as an additive(s).

(1-2) "NWSP"

The term "NWSP" is an acronym for Non-Woven Standard Procedures-Edition 2015. The "NWSP" is the standard of the evaluation method for a nonwoven fabric and a product including the nonwoven fabric, jointly published by European Disposables and Nonwovens Associations (EDANA) and Association of the Nonwoven Fabrics Industry (INDA) and commonly employed in Europe and the U.S.A. The NWSP also describes the standardized measurement methods for water-absorbing resins. Herein, the physical properties of a water-absorbing resin are measured in compliance with the first edition of NWSP (2015). Note that, herein, various physical properties of the water-absorbing resin are measured by the measurement methods employed in the later-described Examples, unless otherwise noted.

[2] Water-Absorbing Resin

A water-absorbing resin comprised by an absorbent article produced by a production method in accordance with an embodiment of the present invention is a particulate poly (meth)acrylic acid (salt)-based water-absorbing resin, the water-absorbing resin containing water-soluble polyalkylene glycol having a weight average molecular weight of not more than 2000, the water-absorbing resin substantially not including a liquid permeability enhancer, the water-absorbing resin satisfying (1) to (5) below:

(1) a centrifuge retention capacity (CRC) of not less than 20 g/g and not more than 35 g/g;

(2) an absorption against pressure (AAP), measured under load of 0.7 psi, of not less than 25 g/g;

(3) a saline flow conductivity (SFC) of not less than 15 (×10-7 cm3·sec/g);

(4) a free swell rate (FSR) of not less than 0.33 g/(g s); and (5) an initial water absorption speed under load (T20) of not more than 145 seconds.

The inventors of the present invention made diligent studies to attain the object, and found that a water-absorbing resin produced to contain water-soluble polyalkylene glycol of a specific molecular weight can achieve an improved initial water absorption speed under load (T20) even substantially without a liquid permeability enhancer added thereto. Based on this finding, the inventors of the present invention completed the present invention. The initial water absorption speed under load (e.g., T20) gives influences to liquid absorbency or re-wet of an absorbent article. For example, an absorbent article (e.g., a paper diaper) produced to include the water-absorbing resin having a fast initial water absorption speed under load (e.g., T20) can quickly absorb a discharged liquid such as urine and can suppress or reduce exuding (re-wet) of the discharged liquid. Furthermore, the liquid permeability enhancer is not added to the above-described water-absorbing resin. This makes it possible to suppress or reduce problems involving dust, such as dusting and/or filter clogging that may otherwise occur during production of the water-absorbing resin and in a production line of paper diapers.

[2-1] Poly(Meth)Acrylic Acid (Salt)-Based Water-Absorbing Resin

In an embodiment of the present invention, a "poly(meth) acrylic acid (salt)-based water-absorbing resin" means a hydrophilic crosslinked polymer obtained by polymerizing and crosslinking a monomer composition containing a (meth)acrylic acid (salt)-based monomer.

The "(meth)acrylic acid (salt)" herein means (meth) acrylic acid and/or a salt thereof. The "monomer composition containing the (meth)acrylic acid (salt)-based monomer" herein means a monomer composition containing the (meth)acrylic acid (salt) by not less than 50 mol % relative to the whole of the monomers excluding a crosslinking agent.

In other words, the poly(meth)acrylic acid (salt)-based water-absorbing resin is a crosslinked polymer that contains a structural unit derived from (meth)acrylic acid (salt) by not less than 50 mol % relative to the whole of the structural units constituting the poly(meth)acrylic acid (salt)-based water-absorbing resin and that may optionally further contain a graft component.

The poly(meth)acrylic acid (salt)-based water-absorbing resin is a crosslinked polymer made of a raw material containing (meth)acrylic acid (salt) by not less than 50 mol %, preferably not less than 70 mol %, more preferably not less than 90 mol %, and preferably not more than 100 mol %, more preferably substantially 100 mol %, relative to a part of the monomer(s) involving the polymerization reaction which part does not include the internal crosslinking agent.

A water-absorbing resin comprised by an absorbent article produced by a production method in accordance with an embodiment of the present invention is in particulate form. The water-absorbing resin in particulate form (particulate water-absorbing resin) may have a non-uniformly pulverized shape (non-uniform shape), a spherical shape, a fiber shape, a bar shape, a substantially spherical shape, or a flat shape, for example. Among these, the particulate water-absorbing resin is preferably at least partially in the form of a non-uniformly pulverized shape, from among the above-described shapes. In consideration of applications to absorbent articles such as paper diapers for infants, the water-absorbing resin more preferably has a non-uniform shape, among the above-described particle shapes, from the viewpoints of the diffusivity of liquid (urine), a low possibility of falling-off from pulps, and the like. The concept “particulate water-absorbing resin” encompasses both a single particle of the particulate water-absorbing resin and an aggregate of a plurality of particles of the water-absorbing resin. The expressions “in particulate form” and “particulate” each refer to the form of particles. The “particle” refers to a solid or liquid particulate minute object having a measurable size (Glossary of Technical Terms in Japanese Industrial Standards, the fourth edition, page 2002).

<Monomers>

The “monomer” refers to a raw material component (monomer) constituting the water-absorbing resin (polymer). Examples of the “monomer” encompass a monomer other than the (meth)acrylic acid (salt)-based monomer and an internal crosslinking agent, in addition to the (meth) acrylic acid (salt)-based monomer that is a main component. That is, the whole of the monomers constituting the water-absorbing resin is a monomer composition. Examples of the (meth)acrylic acid (salt)-based monomer encompass (meth) acrylic acid and a salt thereof.

The monomer other than the (meth)acrylic acid (salt)-based monomer is preferably a monomer containing an acid group, among monomers (ethylenically unsaturated monomers) having an unsaturated double bond. Specific examples of such a monomer encompass anionic unsaturated monomers such as maleic acid (maleic anhydride), fumaric acid, crotonic acid, itaconic acid, cinnamic acid, vinyl sulfonic acid, allyl toluene sulfonic acid, vinyl toluene sulfonic acid, styrene sulfonic acid, 2-(meth)acrylic amido-2-methyl propanesulfonate, 2-(meth)acryloyl ethane sulfonic acid, 2-(meth)acryloyl propane sulfonic acid, and 2-hydroxyethyl (meth)acryloyl phosphate and/or salts thereof. One kind of these monomers may be used alone, or two or more kinds may be used in combination, as needed.

Examples of the salt encompass an alkali metallic salt, an ammonium salt, and an amine salt. The salt is more preferably a sodium salt, a potassium salt, a lithium salt, or an ammonium salt, and particularly preferably a sodium salt.

The monomer composition containing the (meth)acrylic acid (salt)-based monomer is preferably neutralized by 10 mol % to 90 mol %, more preferably by 40 mol % to 80 mol %, particularly preferably by 60 mol % to 75 mol %.

Thus, the monomer composition containing the (meth) acrylic acid (salt)-based monomer is preferably neutralized with a neutralizing liquid containing a basic compound such as a hydroxide of alkali metal such as sodium hydroxide, potassium hydroxide, or lithium hydroxide; a (hydrogen) carbonate salt such as a sodium (hydrogen) carbonate or potassium (hydrogen) carbonate; or ammonia. Particularly preferably, the above monomer composition is neutralized with a neutralizing liquid containing sodium hydroxide.

In addition to the above-described monomers such as the “(meth)acrylic acid (salt)-based monomer” and the “monomer other than the (meth)acrylic acid (salt)-based monomer”, the monomer composition may further contain a “hydrophilic or hydrophobic unsaturated monomer (hereinafter, referred to as an “additional monomer”)”, as necessary. Examples of the additional monomer encompass: unsaturated monomers containing a mercaptan group; unsaturated monomers containing a phenolic hydroxyl group; unsaturated monomers containing an amide group, such as N-vinyl-2-pyrrolidone, N-vinyl acetamide, (meth) acrylamide, N-isopropyl(meth)acrylamide, N-ethyl(meth) acrylamide, and N,N-dimethyl(meth)acrylamide; and unsaturated monomers containing an amino group, such as N,N-dimethylaminoethyl(meth)acrylate, N,N-dimethylaminopropyl(meth)acrylate, and N,N-dimethylaminopropyl (meth)acrylamide. The amount of the additional monomer to be used may be an amount with which the physical properties of the water-absorbing resin to be obtained would not be impaired. Specifically, the amount of the additional monomer to be used is not more than 50 mol %, more preferably not more than 20 mol %, relative to a part of the monomer composition not including the internal crosslinking agent.

<Internal Crosslinking Agent>

The water-absorbing resin is internally crosslinked by an internal crosslinking agent.

Examples of the internal crosslinking agent encompass N,N'-methylene-bis(meth)acrylamide, (poly)ethylene glycol di(meth)acrylate, (poly)propylene glycol di(meth)acrylate, trimethylolpropane di(meth)acrylate, trimethylolpropane tri (meth)acrylate, glycerin tri(meth)acrylate, glycerin acrylate methacrylate, ethylene oxide modified trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth) allyloxyalkane, (poly)ethylene glycol diglycidyl ether, glycerol diglycidyl ether, ethylene glycol, polyethylene glycol, propylene glycol, glycerin, pentaerythritol, ethylene diamine, polyethyleneimine, and glycidyl (meth)acrylate. At least one kind is selected from these internal crosslinking agents, in consideration of the reactivity and/or the like.

In an embodiment of the present invention, selected as the internal crosslinking agent is preferably an internal crosslinking agent having two or more polymerizable unsaturated groups, more preferably an internal crosslinking agent having two or more polymerizable unsaturated groups having a (poly)alkylene glycol structure, from the viewpoints of the water absorption performance and the like of the water-absorbing resin. Specific examples of the polymerizable unsaturated group encompass an allyl group and a (meth) acrylate group. Of these, the (meth)acrylate group is preferable. Examples of the internal crosslinking agent having two or more polymerizable unsaturated groups having the (poly)alkylene glycol structure encompass polyethylene glycol di(meth)acrylate. The number (hereinafter, indicated by “n”) of alkylene glycol units is preferably not less than one, more preferably not less than two, even more preferably not less than four, particularly preferably not less than six, and preferably not more than 100, more preferably not more than 50, even more preferably not more than 20, particularly preferably not more than 10.

The amount of the internal crosslinking agent to be used is preferably not less than 0.0001 mol %, more preferably not less than 0.001 mol %, even more preferably not less than 0.01 mol %, and preferably not more than 10 mol %, more preferably not more than 5 mol %, even more preferably not more than 1 mol %, relative to a part of the monomer composition not including the internal crosslinking agent. Setting the used amount of the internal crosslinking agent so as to fall within the above range can yield a water-absorbing resin having a desired water absorption performance. Meanwhile, setting the used amount of the internal crosslinking agent outside the above range results in a reduction in the gel strength, thereby causing an increase in the water-soluble content and/or a reduction in the absorption capacity.

<Surface-Crosslinking Agent>

A water-absorbing resin comprised by an absorbent article produced by a production method in accordance with an embodiment of the present invention is surface-crosslinked. A surface-crosslinking agent used therefor may be any of the surface-crosslinking agents described in U.S. Pat. No. 7,183,456. At least one kind is selected from these surface-crosslinking agents, in consideration of the reactivity and/or the like. From the viewpoints of the ease of handling of the surface-crosslinking agent, the water absorption performance of the water-absorbing resin, and the like, it is preferable to select a surface-crosslinking agent that has two or more functional groups reactive to a carboxyl group and that is an organic compound forming a covalent bond.

Specific examples of the surface-crosslinking agent encompass: polyhydric alcohol compounds such as ethylene glycol, diethylene glycol, triethylene glycol, tetraethylene glycol, polyethylene glycol, propylene glycol, dipropylene glycol, polypropylene glycol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,3-hexanediol, 2,4-hexanediol, glycerin, polyglycerin, diethanolamine, and triethanolamine; polyamine compounds such as ethylenediamine, diethylenetriamine, triethylenetetramine, tetraethylenepentamine, pentaethylenehexamine, polyallylamine, and polyethyleneimine; haloepoxy compounds and a condensate of a polyamine compound and a haloepoxy compound; oxazoline compounds such as 1,2-ethylene bisoxazoline; oxazolidinone compounds; alkylene carbonate compounds such as 1,3-dioxolane-2-one(ethylene carbonate), 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; polyfunctional glycidyl compounds such as ethylene glycol diglycidyl ether, polyethylene diglycidyl ether, propylene glycol diglycidyl ether, polypropylene glycol diglycidyl ether, glycerol polyglycidyl ether, diglycerol polyglycidyl ether, polyglycerol polyglycidyl ether, and glycidol; oxetane compounds; vinyl ether compounds; and cyclic urea compounds. One kind of these may be used alone, or two or more kinds may be used in combination.

More preferably, a water-absorbing resin comprised by an absorbent article produced by a production method in accordance with an embodiment of the present invention includes a surface-crosslinked water-absorbing resin having a non-uniformly pulverized shape. This is preferable because this can provide a water absorption performance under load and a low possibility of falling-off from pulps. Particularly, a water-absorbing resin comprised by an absorbent article produced by a production method in accordance with an embodiment of the present invention contains the surface-crosslinked water-absorbing resin having a non-uniformly pulverized shape preferably by not less than 50 mass %, more preferably not less than 70 mass %, even more preferably not less than 90 mass %, relative to the entire water-absorbing resin.

[2-2] Polyalkylene Glycol

In a water-absorbing resin comprised by an absorbent article produced by a production method in accordance with an embodiment of the present invention, water-soluble polyalkylene glycol having a weight average molecular weight of not more than 2000 is contained. The expression "polyalkylene glycol is contained in the water-absorbing resin" herein means a state where the polyalkylene glycol resides inside the water-absorbing resin. In this state, the polyalkylene glycol only needs to reside inside the water-absorbing resin in its major part, and a part of the polyalkylene glycol may reside in a surface of the water-absorbing resin. That is, provided that the polyalkylene glycol does not reside only in or close to the surface, a part of the polyalkylene glycol may reside in the surface.

Examples of the polyalkylene glycol encompass polyalkylene glycol having a structure expressed by the following general formula (1).

$$H—(OR)n\text{-}OH \qquad (1).$$

In the general formula (1), R is a C2-4 alkylene group that may be in a linear chain form or a branched chain form. In the general formula (1), the average of n is 4 to 50, more preferably 6 to 15.

In the general formula (1), oxyalkylene groups (—OR—) in one molecule may be identical to each other or may be two or more different kinds. More specific examples of the polyalkylene glycol encompass polyethylene glycol, polypropylene glycol, a polyethylene glycol-polypropylene glycol copolymer, and a polyethylene glycol-polypropylene glycol-polybutylene glycol copolymer. One kind of these polyalkylene glycols may be used alone, or two or more kinds may be used in combination.

In one embodiment of the present invention, the polyalkylene glycol is water-soluble. The expression "water-soluble" herein means that not less than 5 g, more preferably not less than 10 g of a substance can be dissolved in 100 g of water at 25° C. The polyalkylene glycol having the water solubility can be dissolved in an aqueous monomer solution, and therefore can be contained in the water-absorbing resin in a suitable manner.

The polyalkylene glycol used in the embodiment of the present invention has a weight average molecular weight of not more than 2000. By selecting the polyalkylene glycol having a weight average molecular weight of not more than 2000, the water-absorbing resin containing it can achieve an improved initial water absorption speed under load. The weight average molecular weight of the polyalkylene glycol is preferably not less than 200, more preferably not less than 300, even more preferably not less than 400. The weight average molecular weight is more preferably not more than 1500, even more preferably not more than 1000. Note that the weight average molecular weight of the polyalkylene glycol is a value measured by gel permeation chromatography.

The content of the polyalkylene glycol in the water-absorbing resin is preferably 0.01 mass % to 1 mass %, relative to the entire water-absorbing resin. Setting the content of the polyalkylene glycol so as to fall within a range of 0.01 mass % to 1 mass % can give, to the water-absorbing resin, an excellent initial water absorption speed under load (e.g., T20). The content of the polyalkylene glycol is more preferably not less than 0.05 mass %, even more preferably not less than 0.10 mass %, further more preferably not less than 0.15 mass %, still more preferably not less than 0.20 mass %. The content of the polyalkylene glycol is more preferably not more than 0.80 mass %, even more preferably not more than 0.60 mass %, particularly preferably not more than 0.40 mass %.

The content of the polyalkylene glycol contained in the water-absorbing resin can be determined by extracting a water-soluble component from the water-absorbing resin and analyzing the extract by liquid chromatography. The extraction method is not limited to any particular one, and may be selected from known methods. It is possible to demonstrate that the polyalkylene glycol is contained in the water-absorbing resin by confirming that the polyalkylene glycol exhibits equal contents in various particle size ranges and has no particle size dependency when the water-absorbing resin is classified into the various particle size ranges and the contents thereof are analyzed in the various particle size ranges. The demonstration is supported by the following fact. That is, in a state where the polyalkylene glycol resides in the surface of the water-absorbing resin, the content of the polyalkylene glycol in the small-particle-size water-absorbing resin is larger than the content of the polyalkylene glycol in the large-particle-size water-absorbing resin. Meanwhile, in a state where the polyalkylene glycol is contained in the water-absorbing resin, the content of the polyalkylene glycol is uniform over the various particle sizes.

[2-3] Liquid Permeability Enhancer

A water-absorbing resin comprised by an absorbent article produced by a production method in accordance with an embodiment of the present invention substantially does not include a liquid permeability enhancer. The expression "substantially does not include" herein refers to a state where the liquid permeability enhancer is not included or a state where the liquid permeability enhancer is included but the content of the liquid permeability enhancer is less than 0.1 mass % (preferably less than 0.001 mass %) relative to the entire water-absorbing resin. A water-absorbing resin including the liquid permeability enhancer by not less than 0.1 mass % tends to exhibit degraded physical properties, such as a lower absorption capacity and/or a lower water absorption speed. In an embodiment of the present invention, it is possible to improve the initial water absorption speed under load (e.g., T20) of the water-absorbing resin, even without adding the liquid permeability enhancer. Furthermore, it is possible to suppress or reduce problems involving dust, such as dusting and/or filter clogging that may otherwise occur during production of the water-absorbing resin and in a production line of paper diapers.

The liquid permeability enhancer is a spacer (support) holding spaces between particles of the water-absorbing resin even under load. Examples of the liquid permeability enhancer encompass a liquid permeability enhancer containing a cationic polymer and a liquid permeability enhancer containing an inorganic substance. Examples of the liquid permeability enhancer containing the inorganic substance encompass a polyvalent metal salt and water-insoluble inorganic particles. The polyvalent metal salt contains divalent or more metal cation, preferably trivalent or more metal cation. Examples of the trivalent or more metal cation encompass aluminum, zirconium, and titanium. Examples of the polyvalent metal salt encompass polyvalent metal compounds such as inorganic salts of polyvalent metals, e.g., aluminum sulfate, aluminum chloride, zirconium chloride oxide, ammonium zirconium carbonate, potassium zirconium carbonate, potassium zirconium carbonate, zirconium sulfate, zirconium chloride hydroxide, and zirconium nitrate, and organic salts of polyvalent metals, e.g., aluminum acetate, aluminum lactate, zirconium acetate, titanium triethanol aminate, and titanium lactate.

Examples of the water-insoluble inorganic particles encompass: water-insoluble inorganic powder in the form of fine particles of, e.g., silicon dioxide, titanium dioxide, aluminum oxide, magnesium oxide, zinc oxide, talc, metal phosphate (such as calcium phosphate, barium phosphate, and aluminum phosphate), metal borate (such as titanium borate, aluminum borate, iron borate, magnesium borate, manganese borate, and calcium borate), a silicic acid or its salt, clay, diatomite, zeolite, bentonite, kaolin, hydrotalcite, and activated clay; and organic fine powder of, e.g., calcium lactate, aluminum lactate, and metallic soap (polyvalent metal salts of long-chain fatty acids). Typically, the inorganic fine particles have a volume-average particle diameter of not more than 10 μm. In the present embodiment, it is possible to obtain a water-absorbing resin having an improved initial water absorption speed under load (e.g., T20), substantially without adding any of these polyvalent metal salts and water-insoluble inorganic particles.

[2-4] Physical Properties of Water-Absorbing Resin

A water-absorbing resin comprised by the absorbent article produced by a production method in accordance with an embodiment of the present invention has a centrifuge retention capacity (CRC) of preferably not less than 20 g/g, more preferably not less than 25 g/g, even more preferably not less than 28 g/g, particularly preferably not less than 29 g/g. A higher upper limit of the CRC is more preferable. However, in consideration of a balance between the CRC and other physical properties, the CRC is preferably not more than 35 g/g, more preferably not less than 32 g/g, even more preferably not more than 31 g/g, particularly preferably not more than 30 g/g.

A water-absorbing resin comprised by the absorbent article produced by a production method in accordance with an embodiment of the present invention has an absorption against pressure (AAP), measured under load of 0.7 psi, of preferably not less than 25 g/g, more preferably not less than 25.2 g/g, even more preferably not less than 25.4 g/g, particularly preferably not less than 25.6 g/g, most preferably not less than 25.8 g/g. The upper limit of the AAP is not particularly limited. However, in consideration of a balance between the AAP and other physical properties, the AAP is preferably not less than 30 g/g.

In a case where the AAP is set so as to be not less than 25 g/g, the amount of a liquid going out from an absorbent body (generally, the amount of such a liquid is referred to as "re-wet") when a pressure is applied to the absorbent body is not so large. Therefore, the absorbent body having an AAP of not less than 25 g/g is suitably applicable to an absorbent article such as a paper diaper. Note that the AAP can be controlled by the particle size, the surface-crosslinking agent, and/or the like.

A water-absorbing resin comprised by the absorbent article produced by a production method in accordance with an embodiment of the present invention has a saline flow conductivity (SFC) of preferably not less than 15×10-7 cm3·sec/g, more preferably not less than 18×10-7 cm3·sec/g, even more preferably not less than 20×10-7 cm3·sec/g, particularly preferably not less than 30×10-7 cm3·sec/g. A higher upper limit of the SFC is more preferable. There is no particular limitation on the upper limit of the SFC.

A water-absorbing resin comprised by the absorbent article produced by a production method in accordance with an embodiment of the present invention has a free swell rate (FSR) of preferably not less than 0.33 g/(g s), more preferably not less than 0.36 g/(g s), even more preferably not less than 0.39 g/(g s), particularly preferably not less than 0.42 g/(g s). The FSR is related to the surface area and the non-uniformly pulverized particle shape of the water-absorbing resin. It is assumed that a water-absorbing resin having a higher FSR has a larger surface area and/or a more non-uniformly pulverized particle shape (i.e., a particle shape that is more dissimilar from a spherical shape).

A water-absorbing resin comprised by the absorbent article produced by a production method in accordance with an embodiment of the present invention has an initial water absorption speed under load (T20) that can be not more than 145 seconds. The T20 is preferably not more than 140 seconds, more preferably not more than 135 seconds, even more preferably not more than 130 seconds, not more than 120 seconds, not more than 110 seconds, not more than 100 seconds. By setting the T20 so as to fall within the above range in the water-absorbing resin that is applied to, e.g., an absorbent article such as a paper diaper, the absorbent article can quickly absorb a discharged liquid such as urine, and can suppress or reduce exuding (re-wet) of the discharged liquid.

A production method in accordance with an embodiment of the present invention polymerizes a monomer and generates a crosslinked hydrogel polymer containing specific polyalkylene glycol during or after the polymerization to produce a water-absorbing resin containing the specific polyalkylene glycol, adjusts CRC of the crosslinked hydrogel (gel CRC) to be within a given range, and controls various physical properties (CRC, AAP, SFC, FSR) of the final water absorbing resin to be within prescribed ranges. Consequently, it is possible to produce a water-absorbing resin having a small T20 value and an excellent initial water absorption speed under load. In other words, a water-absorbing resin that is obtained by the above-described production method and that has various physical properties being within the above ranges has a small T20 value and an excellent initial water absorption speed under load. Note that the various physical properties can be controlled by, e.g., the particle size, particle shape, and/or surface-crosslinking of the water-absorbing resin.

Among the physical properties of the water absorbing resin, AAP (0.7)/SFC* is preferably not less than 0.2, not less than 0.3, not less than 0.4, not less than 0.5, not less than 0.6, not less than 0.7, and more preferably not more than 5.0, not more than 4.0, not more than 3.0, not more than 2.0, not more than 1.5, not more than 1.3. Here, SFC*=SFC/(1×10-7).

A water-absorbing resin comprised by the absorbent article produced by a production method in accordance with an embodiment of the present invention preferably has an initial water absorption speed under load (T15) of not more than 90 seconds. The T15 is more preferably not more than 80 seconds, even more preferably not more than 75 seconds, still more preferably not more than 70 seconds. By setting the T15 so as to fall within the above range in the water-absorbing resin that is applied to, e.g., an absorbent article such as a paper diaper, the absorbent article can quickly absorb a discharged liquid such as urine, thereby suppressing or reducing exuding (re-wet) of the discharged liquid.

A water-absorbing resin comprised by the absorbent article produced by a production method in accordance with an embodiment of the present invention preferably has an initial water absorption speed under load (T10) of not more than 50 seconds. The T10 is more preferably not more than 46 seconds, even more preferably not more than 43 seconds, still more preferably not more than 40 seconds. By setting the T10 so as to fall within the above range in the water-absorbing resin that is applied to an absorbent article such as a paper diaper, the absorbent article can quickly absorb a discharged liquid such as urine, thereby suppressing or reducing exuding (re-wet) of the discharged liquid.

A water-absorbing resin comprised by the absorbent article produced by a production method in accordance with an embodiment of the present invention preferably has an initial water absorption speed under load (T5) of not more than 25 seconds. The T5 is more preferably not more than 22 seconds, even more preferably not more than 21 seconds, still more preferably not more than 19 seconds. By setting the T5 so as to fall within the above range in the water-absorbing resin that is applied to, e.g., an absorbent article such as a paper diaper, the absorbent article can quickly absorb a discharged liquid such as urine, thereby suppressing or reducing exuding (re-wet) of the discharged liquid.

The sum (T5+T10+T15) of the initial water absorption speeds under load (T5, T10, T15) of a water-absorbing resin comprised by an absorbent article produced by a production method in accordance with an embodiment of the present invention is preferably not more than 160 seconds, more preferably not more than 140 seconds, even more preferably not more than 135 seconds, particularly preferably not more than 130 seconds. By setting the value of T5+T10+T15 so as to fall within the above range in the water-absorbing resin that is applied to an absorbent article such as a paper diaper, the absorbent article can quickly absorb a discharged liquid such as urine, thereby suppressing or reducing exuding (re-wet) of the discharged liquid.

A water-absorbing resin comprised by the absorbent article produced by a production method in accordance with an embodiment of the present invention has a moisture content of, e.g., not more than 15 mass %, preferably not more than 10 mass %, more preferably not more than 5 mass %, even more preferably not more than 3 mass %, particularly preferably not more than 1 mass %, particularly preferably substantially 0 mass %. The moisture content is controlled by carrying out drying or surface-crosslinking and, if necessary, addition of water or further drying to attain the given moisture content described above, for example. Setting the moisture content so as to be not more than 15 mass % can suppress or reduce coloration as well as adhesiveness and reduction of the absorption capacity of the water-absorbing resin. Furthermore, setting the moisture content so as to be not more than 15 mass % can suppress or reduce a reduction in the initial water absorption speeds under load (T20, T5, T10, T15) in the water-absorbing resin.

[3] Method for Producing Water-Absorbing Resin

A method in accordance with an embodiment of the present invention for producing an absorbent article comprising a water-absorbing resin is a method comprising the production of a surface-crosslinked particulate poly(meth) acrylic acid (salt)-based water-absorbing resin, the method comprising the steps of:

(i) preparing a (meth)acrylic acid (salt)-based aqueous monomer solution;
(ii) polymerizing the (meth)acrylic acid (salt)-based aqueous monomer solution;
(iii) carrying out gel-crushing of a crosslinked hydrogel polymer generated during or after the polymerization to obtain a particulate hydrogel;
(iv) drying the particulate hydrogel to obtain a dried polymer;
(v) pulverizing and/or classifying the dried polymer to obtain a particulate water-absorbing resin before surface-crosslinking;
(vi) surface-crosslinking the particulate water-absorbing resin before surface-crosslinking; and
(vii) incorporating the surface-crosslinked particulate water-absorbing resin in an absorbent article, wherein in the step (i) and/or the step (ii), water-soluble polyalkylene glycol having a weight average molecular weight of not more than 2000 is added to the aqueous monomer solution so that a total amount of the water-soluble polyalkylene glycol added in the step (i) and/or the step (ii) is 0.01 mass % to 1 mass % relative to a total mass of a monomer included in the aqueous monomer solution, the crosslinked hydrogel polymer has a centrifuge retention capacity of not more than 31 g/g and not less than 20 g/g, and the surface-crosslinked particulate poly(meth)acrylic acid (salt)-based water-absorbing resin obtained by said method satisfies (1) to (4) below:

(1) a centrifuge retention capacity (CRC) of not less than 20 g/g and not more than 35 g/g;

(2) an absorption against pressure (AAP), measured under a load of 0.7 psi, of not less than 25 g/g;

(3) a saline flow conductivity (SFC) of not less than 15 (×10-7 cm3·sec/g); and (4) a free swell rate (FSR) of not less than 0.33 g/(g s).

That is, in the method in accordance with the embodiment of the present invention for producing an absorbent article comprising the water-absorbing resin, the water-soluble polyalkylene glycol having a weight average molecular weight of not more than 2000 is added in the step (i) of preparing the (meth)acrylic acid (salt)-based aqueous monomer solution or the step (ii) of polymerizing the (meth) acrylic acid (salt)-based aqueous monomer solution. Alternatively, the polyalkylene glycol may be added in both the steps (i) and (ii). Consequently, it is possible to produce the water-absorbing resin containing the polyalkylene glycol.

The method for adding the polyalkylene glycol is not limited to any particular one. The polyalkylene glycol may be directly added in an aqueous monomer solution or in a mixture during polymerization. Alternatively, the polyalkylene glycol may be added in a solution, particularly in an aqueous solution.

The centrifuge retention capacity of the crosslinked hydrogel polymer generated during or after the polymerization in the step (ii) has an upper limit of not more than 31 g/g, preferably not more than 30 g/g, and a lower limit of not less than 20 g/g, preferably not less than 25 g/g. It is expected that setting, in the crosslinked hydrogel polymer containing the polyalkylene glycol, the centrifuge retention capacity so as to fall within a given range will lead to production of a water-absorbing resin having the later-described form. Consequently, the water-absorbing resin is assumed to have, e.g., a lower T20 value and an improved initial water absorption speed under load. A method for measuring the centrifuge retention capacity of the crosslinked hydrogel polymer will be described later.

The method in accordance with the embodiment of the present invention for producing an absorbent article comprising the water-absorbing resin can include a step of checking whether or not the crosslinked hydrogel polymer that is to be subjected to the gel-crushing in the step (iii) is a crosslinked hydrogel polymer having a centrifuge retention capacity being within the above-described range. The method for checking whether or not the centrifuge retention capacity of the crosslinked hydrogel polymer is within the above-described range may be, for example, a method for cutting out a portion of the crosslinked hydrogel polymer generated during or after the polymerization in the step (ii) so that the portion of the crosslinked hydrogel polymer is used as a sample for checking, measuring a centrifuge retention capacity of the sample for checking, and checking whether or not the measured value of the centrifuge retention capacity is within the above-described range. Note that, after the value of the centrifuge retention capacity of the sample for checking is confirmed to be within the above-described range, the remaining portion of the crosslinked hydrogel polymer which has not been used for the measurement of the centrifuge retention capacity is subjected to gel-crushing so that the gel-crushing in the step (iii) is carried out. Alternatively, in a case where the steps (i) and (ii) are carried out under a condition confirmed in advance to enable production of a crosslinked hydrogel polymer having a value of an centrifuge retention capacity within the above-described range, the gel-crushing in the step (iii) may be carried out without checking the centrifuge retention capacity of the sample for checking.

Aggregation

By setting the centrifuge retention capacity of the crosslinked hydrogel polymer so as to fall within a given range, the crosslinked hydrogel polymer can achieve somewhat high strength. The crosslinked hydrogel polymer forms a secondary aggregate through aggregation of primary particles during the gel-crushing step. In this regard, considering that the crosslinked hydrogel polymer as the primary particles has high strength and is thus not easily deformed and the crosslinked hydrogel polymer contains specific polyalkylene glycol, the secondary aggregate is assumed to have many portions where the primary particles are loosely bonded to each other. Similarly to the above-described secondary aggregate, the water-absorbing resin indicated in the embodiment of the present invention that can be obtained by gel-crushing, drying, pulverizing and/or classifying, and surface-crosslinking of the crosslinked hydrogel polymer is also assumed to have many portions where the primary particles are loosely bonded to each other. Here, it is assumed that the portions where the particles are loosely bonded to each other have a void(s). Even if such a void(s) cannot be confirmed therein, it is believed that these portions have capacity to absorb a liquid such as water. The water-absorbing resin indicated in the embodiment of the present invention is assumed to have a form having many portions that have capacity to absorb a liquid such as water and thereby having a smaller T20 value and an improved initial water absorption speed under load.

Other than the above, it is necessary to set various physical properties (CRC, AAP, SFC, FSR) of the final water-absorbing resin within the prescribed ranges. With this, in a water-absorbing resin comprised by an absorbent article to be produced, it is possible to improve an initial water absorption speed under load of the water-absorbing resin and to reduce a T20 value of the water-absorbing resin so as to be as small as not more than 145 seconds, for example.

The amount of the polyalkylene glycol to be added is 0.01 mass % to 1 mass %, relative to the total mass of the monomers included in the aqueous monomer solution. Setting the added amount of the polyalkylene glycol so as to fall within a range of 0.01 mass % to 1 mass % yields a water-absorbing resin having an excellent initial water absorption speed under load (e.g., T20). The added amount of the polyalkylene glycol is preferably not less than 0.05 mass %, more preferably not less than 0.10 mass %, even more preferably not less than 0.15 mass %, particularly preferably not less than 0.20 mass %. The added amount of the polyalkylene glycol is preferably not more than 0.80 mass %, more preferably not more than 0.60 mass %, even more preferably not more than 0.40 mass %. The added amount of the polyalkylene glycol is preferably adjusted so that the content of the polyalkylene glycol is 0.01 mass % to 1 mass % with respect to the entire surface-crosslinked particulate poly(meth)acrylic acid (salt)-based water-absorbing resin.

The poly(meth)acrylic acid (salt)-based water-absorbing resin, the polyalkylene glycol, the liquid permeability enhancer, and the physical properties of the water-absorbing resin obtained are as those described in "[2] Water-absorbing resin".

[3-1] (Meth)Acrylic Acid (Salt)-Based Aqueous Monomer Solution Preparation Step (Step (i))

This step is a step of preparing an aqueous solution that is a raw material (a monomer composition; particularly, the one containing a (meth)acrylic acid (salt)-based monomer as a main component and at least one kind of internal crosslinking agent) from which a water-absorbing resin (polymer) is made. Note that a slurry liquid of the monomer composition may be used. However, for convenience, a description herein deals with a case where an aqueous solution of the monomer composition is used.

(Monomer)

As described in "[Poly(meth)acrylic acid (salt)-based water-absorbing resin]" above, the monomers used in this step are raw material components (monomers) forming the water-absorbing resin (polymer), and encompass the (meth)acrylic acid (salt)-based monomer, the monomer other than the (meth)acrylic acid (salt)-based monomer, and the internal crosslinking agent. That is, the whole of the monomers forming the water-absorbing resin correspond to a monomer composition.

(Neutralization with Basic Compound)

As described above, in an embodiment of the present invention, the (meth)acrylic acid (salt) herein is preferably partially neutralized with use of the basic compound. That is, in the embodiment of the present invention, the water-absorbing resin including the poly(meth)acrylic acid having partially neutralized acid groups is preferable.

Examples of the basic compound encompass carbonates and hydrogencarbonates of alkali metals, hydroxides of alkali metals, ammonia, and organic amine. From the viewpoint of the water absorption performance of the water-absorbing resin, a compound having strong basicity is selected from among these. Note that, from the viewpoint of the ease of handling, the basic compound is preferably in the form of an aqueous solution.

The timing to carry out the neutralization may be before, during, or after the polymerization. The neutralization may be carried out at plural timings or plural times. From the viewpoint of the production efficiency of the water-absorbing resin, it is preferable to carry out the neutralization continuously.

As described above, the neutralization rate of the (meth)acrylic acid (salt) in an embodiment of the present invention is preferably not less than 10 mol %, more preferably not less than 40 mol %, even more preferably not less than 50 mol %, particularly preferably not less than 60 mol %, and preferably not more than 90 mol %, more preferably not more than 85 mol %, even more preferably not more than 80 mol %, particularly preferably not more than 75 mol %, relative to the acid groups of the monomer composition. Setting the neutralization rate so as to fall within the above range can suppress or reduce degradation in the water absorption performance of the water-absorbing resin. Note that the neutralization rate is applied to any of the neutralization before the polymerization, the neutralization during the polymerization, and the neutralization after the polymerization. The neutralization rate is applied also to the water-absorbing resin.

(Internal Crosslinking Agent)

The internal crosslinking agent and the amount of the internal crosslinking agent to be used in this step are as described in "[Poly(meth)acrylic acid (salt)-based water-absorbing resin]" above.

In an embodiment of the present invention, the timing to add the internal crosslinking agent only needs to be the one with which the polymer can be uniformly crosslinked. For example, the internal crosslinking agent may be added to an aqueous solution of the monomer composition before the polymerization or to a hydrogel during or after the polymerization. Particularly preferable is a method of preliminarily adding a given amount of the internal crosslinking agent to the aqueous solution of the monomer composition.

(Polyalkylene Glycol)

In a preferable embodiment of the present invention, the polyalkylene glycol can be added to the aqueous solution of the monomer composition. The addition of the polyalkylene glycol may be carried out in the later-described polymerization step. The amount of the polyalkylene glycol to be added is as described above. Particularly, it is preferable to add the polyalkylene glycol in the step of preparing the aqueous solution of the monomer composition.

(Additional Substance to be Added to Aqueous Solution of Monomer Composition)

In an embodiment of the present invention, in order to improve the physical properties of the water-absorbing resin, an additional substance described below can be added to the aqueous solution of the monomer composition, to the solution that is in the process of the reaction, or to the solution that is after the reaction, at at least one of a timing of preparation of the aqueous solution of the monomer composition, a timing during a period in which the polymerization reaction and the crosslinking reaction are being carried out, and a timing after the polymerization reaction and the crosslinking reaction are carried out.

Examples of the additional substance encompass: hydrophilic polymers such as starch, a starch derivative, cellulose, a cellulose derivative, polyvinyl alcohol (PVA), polyacrylic acid (salt), existing crosslinked polyacrylic acid (salt); and compounds such as carbonate, an azo compound, a blowing agent causing various bubbles, a surfactant, a chelating agent, and a chain transfer agent.

In a case where the hydrophilic polymer is employed, it is possible to obtain a water-absorbing resin to which the hydrophilic polymer is grafted. For example, it is possible to obtain a polyacrylic acid (salt)-based water-absorbing resin to which starch is grafted or a polyacrylic acid (salt)-based water-absorbing resin to which PVA is grafted. These grafted water-absorbing resins are also encompassed in the scope of the polyacrylic acid (salt)-based water-absorbing resin.

The amount(s) of the additional substance(s) to be added is/are adjusted so as not to impair the effects of the present invention. For example, the total amount of the additional substance(s) to be added is preferably not more than 50 mass %, more preferably not more than 20 mass %, even more preferably not more than 10 mass %, particularly preferably not more than 5 mass %, and preferably not less than 0 mass %, more preferably more than 0 mass %, relative to the aqueous solution of the monomer composition.

(Monomer Component Concentration)

By selecting some of the monomer composition, the polyalkylene glycol, the above-described substances and components (in this section, referred to as "monomer components") according to the purpose and mixing them in amounts within the above ranges, it is possible to prepare an aqueous solution containing all the monomer components (i.e., a mixture of the monomer composition, the polyalkylene glycol, the substances, and the components). Note that, in an embodiment of the present invention, the aqueous solution containing all the monomer components may be replaced with a solution prepared by mixing water containing all the monomer components and a hydrophilic solvent.

From the viewpoint of the physical properties of the water-absorbing resin, the total concentration of the monomer components is preferably not less than 10 mass %, more preferably not less than 20 mass %, even more preferably not less than 30 mass %, and preferably not more than 80 mass %, more preferably not more than 75 mass %, even more preferably not more than 70 mass %. The total concentration of the monomer components can be obtained by adding up the concentrations of the monomer components. The concentration of each monomer component can be calculated according to the following formula (A):

$$\text{Concentration of monomer component(mass \%)} = [(\text{mass of monomer component})/(\text{mass of aqueous solution including all monomer components})] \times 100 \quad \text{formula (A).}$$

In the formula (A), the "mass of aqueous solution including all monomer components" does not include a mass of a hydrophobic organic solvent used in reversed phase suspension polymerization.

[3-2] Polymerization Step (Step (ii))

This step is a step of polymerizing the aqueous monomer solution to obtain a crosslinked hydrogel polymer (hereinafter, simply referred to as a "hydrogel"). Preferably, this step is a step of obtaining a hydrogel by polymerizing the aqueous monomer solution that is obtained in the aqueous monomer solution preparation step and that includes the monomer containing the acrylic acid (salt) as a main component and at least one kind of internal crosslinking agent.

(Polymerization Initiator)

The polymerization initiator used in an embodiment of the present invention may be one kind or two or more kinds selected, according to the type of the monomer that is to be polymerized, the polymerization condition, and/or the like, from the polymerization initiators generally used to produce a water-absorbing resin. Examples of the polymerization initiator encompass a thermal polymerization initiator and a photopolymerization initiator.

Examples of the thermal polymerization initiator encompass: persulfates such as sodium persulfate, potassium persulfate, and ammonium persulfate; peroxides such as hydrogen peroxide, t-butyl peroxide, and methyl ethyl ketone peroxide; and azo compounds such as an azonitrile compound, an azoamidine compound, a cyclic azoamidine compound, an azoamide compound, an alkylazo compound, 2,2'-azobis(2-amidinopropane)dihydrochloride, and 2,2'-azobis [2-(2-imidazoline-2-yl)propane]dihydrochloride.

Examples of the photopolymerization initiator encompass a benzoin derivative, a benzil derivative, an acetophenone derivative, a benzophenone derivative, and an azo compound.

Of these, persulfate is preferable, in consideration of the cost and the residual monomer reduction capability. Alternatively, a redox-type polymerization initiator, obtained by combining the oxidizable polymerization initiator such as the above-described persulfate or peroxide with a reducing agent for promoting decomposition of the oxidizable polymerization initiator may be used. Examples of the reducing agent encompass: (bi)sulfurous acid (salt) such as sodium sulfite and sodium hydrogen sulfite; L-ascorbic acid (salt); reducible metal (salt) such as a ferrous salt; and amines.

The amount of the polymerization initiator to be used is preferably not less than 0.001 mol %, more preferably not less than 0.010 mol %, and preferably not more than 1.000 mol %, more preferably not more than 0.500 mol %, even more preferably not more than 0.100 mol %, relative to the monomers not including the internal crosslinking agent. The amount of the reducing agent to be used is preferably not less than 0.0001 mol %, more preferably not less than 0.0005 mol %, and preferably not more than 0.0200 mol %, more preferably not more than 0.0150 mol %, relative to the monomers not including the internal crosslinking agent. Setting the used amount of each agent so as to fall within the above range can impart a desired water absorption performance to the water-absorbing resin.

Alternatively, in an embodiment of the present invention, the polymerization reaction may be initiated by irradiation of an activated energy ray such as a radial ray, an electron beam, or an ultraviolet ray. Further alternatively, irradiation of the activated energy ray and the above-described polymerization initiator may be employed in combination to initiate the polymerization reaction.

(Form of Polymerization)

A form of polymerization applicable to an embodiment of the present invention may be aqueous solution polymerization, reversed phase suspension polymerization, spray polymerization, droplet polymerization, bulk polymerization, or precipitation polymerization, for example. Of these, from the viewpoints of the ease of polymerization control and the water absorption performance of the water-absorbing resin, the aqueous solution polymerization or the reversed phase suspension polymerization is preferable, and the aqueous solution polymerization is more preferable. The aqueous solution polymerization is explained in Japanese Patent Application Publication Tokukaihei No. 4-255701 (1992), for example. The reversed phase suspension polymerization is explained in International Publication No. WO 2007/004529 and International Publication No. WO 2012/023433, for example.

A preferable form of the continuous aqueous solution polymerization may be high-temperature initiated polymerization, high-concentration polymerization, or foaming polymerization, for example. The "high-temperature initiated polymerization" refers to a form of polymerization in which the temperature of the aqueous monomer solution at the time of starting the polymerization is set preferably at not lower than 35° C., more preferably not lower than 40° C., even more preferably not lower than 45° C., particularly preferably not lower than 50° C., and preferably not higher than a boiling point of the aqueous monomer solution. The "high-concentration polymerization" refers to a form of polymerization in which the concentration of the monomers at the time of starting the polymerization is set preferably at not lower than 30 mass %, more preferably not lower than 35 mass %, even more preferably not lower than 40 mass %, particularly preferably not lower than 45 mass %, and preferably not higher than a saturated concentration of the aqueous monomer solution. The "foaming polymerization" refers to a form of polymerization in which an aqueous monomer solution including a blowing agent or bubbles is polymerized. One of these forms of polymerization may be carried out alone, or two or more may be carried out in combination. The form of the aqueous solution polymerization may be of a batch type or a continuous type. From the viewpoint of the production efficiency, the continuous type is preferable. A form of polymerization to be applied to an embodiment of the present invention is preferably a form of polymerization in which a polymerization reaction is initiated immediately after addition of a polymerization initiator. As such a form of polymerization, a form of polymerization in which a polymerization reaction is initiated within one minute after addition of a polymerization initiator is preferable, for example. In the form of polymerization, it is also preferable that the polymerization reaction ends quickly. As such a form of polymerization, a form of polymerization in which the polymerization reaction ends within one minute after initiation of the polymerization is preferable, for example.

Examples of the continuous-type aqueous solution polymerization encompass the continuous belt polymerization described in, e.g., U.S. Pat. Nos. 4,893,999, 6,906,159, U.S. Pat. Nos. 7,091,253, 7,741,400, and 8,519,212 and Japanese Patent Application Publication Tokukai No. 2005-36100 and the continuous kneader polymerization described in, e.g., U.S. Pat. No. 6,987,151.

In the foaming polymerization, bubbles may be dispersed in any of the following methods. For example, the solubility of a gas dissolved in the aqueous monomer solution is lowered so that the gas is dispersed as bubbles. For another example, a gas is externally introduced so that the gas is dispersed as bubbles. For further another example, a blowing agent is added to the aqueous monomer solution to cause foaming. According to the physical properties of the target water-absorbing resin, two or more kinds of the dispersing methods may be selected and applied in combination.

In the method of externally introducing a gas, the gas may be oxygen, air, nitrogen, carbon dioxide, ozone, or a mixture gas of them, for example. From the viewpoints of the polymerizability and the cost, the gas is preferably an inert gas such as nitrogen or carbon dioxide, more preferably nitrogen.

Examples of the available blowing agent encompass a solution, a dispersion liquid, and powder of a particle diameter of not less than 0.1 μm and not more than 1000.0 μm of an azo compound and organic or inorganic carbonate. Of these, inorganic carbonate is preferable. Specifically, it is possible to use carbonate such as sodium carbonate, ammonium carbonate, or magnesium carbonate or hydrogen carbonate.

Carrying out gel-crushing of a foamed hydrogel obtained as a result of the foaming polymerization facilitates drying. Obtaining the water-absorbing resin in the foamed form can increase the water absorption speed, and also can facilitate fixing of the water-absorbing resin to an absorbent article. It is possible to determine whether or not the water-absorbing resin is in the foamed form by checking the presence or absence of a hole(s) on a surface of the water-absorbing resin with an electron microscope, for example, by checking the presence or absence of a hole(s) having a diameter of not less than 1 μm and not more than 100 μm. The number of holes per particle of the water-absorbing resin is preferably not less than one, more preferably not less than 10, and preferably not more than 10000, more preferably not more than 1000. The number of holes per particle of the water-absorbing resin can be controlled by adjusting the conditions in the foaming polymerization.

[3-3] Gel-Crushing Step (Step (iii))

This step is a step of crushing the hydrogel to obtain a hydrogel in particulate form, and is carried out during and/or after the polymerization step. Specifically, the hydrogel may be crushed in the polymerization step or after the polymerization step. That is, this step is a step of carrying out gel-crushing of the hydrogel to obtain a hydrogel in particulate form (hereinafter, referred to as a "particulate hydrogel"). Note that this step is expressed as "gel-crushing" so as to be discriminated from "pulverizing" in the later-described pulverizing step. The target of the gel-crushing is not limited to the hydrogel obtained in the polymerization step. Unless otherwise noted, the target of the gel-crushing may encompass a granular gel obtained by mixing an aqueous liquid and fine powder collected in the later-described classification step. Unless otherwise noted, this also applies to the other steps.

The gel-crushing means adjusting the size of the hydrogel to a given size with use of, e.g., a kneader, a screw extruder such as a meat chopper, or a gel-crusher such as a cutter mill.

It is preferable to carry out gel-crushing of the hydrogel while adding hot water and/or water vapor to the gel-crusher. Addition of the hot water and/or water vapor can yield a particulate hydrogel having a low adhesiveness and a fine air-permeability, that is, a particulate hydrogel that is easily dried. Therefore, addition of the hot water and/or water vapor is preferable. The temperature of the hot water is preferably not lower than 40° C., more preferably not lower than 50° C., even more preferably not lower than 60° C., and preferably not higher than 100° C.

With regard to the embodiments and/or operating condition(s) of the gel-crushing, the methods for the aqueous solution polymerization described in the documents describing the continuous aqueous solution polymerization are employed. The content of the pamphlet of International Publication No. WO 2011/126079 is also preferably applied to an embodiment of the present invention. Note that, in a case where kneader polymerization is employed as the form of polymerization, the polymerization step and the gel-crushing step are carried out at the same time. By carrying out the gel-crushing step in an embodiment of the present invention, it is possible to yield a water-absorbing resin having a non-uniformly pulverized shape.

The method for producing the absorbent article comprising the water-absorbing resin in accordance with the embodiment of the present invention may further include: a granulation step of mixing an aqueous liquid and fine powder collected in the later-described classification step to yield a granular gel; and a granular-gel adding step of adding the granular gel to the hydrogel, the granular-gel adding step being carried out in at least one of the steps between the gel-crushing step and completion of the drying in the drying step and/or at a timing between these steps. In addition, in the gel-crushing step in accordance with the embodiment of the present invention, it is preferable to appropriately control a gel grinding energy. A particulate hydrogel obtained as a result of gel-crushing carried out at a given gel grinding energy described below leads to production of a water-absorbing resin exhibiting improvement in physical properties, specifically, an absorption speed, e.g., an FSR described in International Publication No. WO 2009/016055 and/or a Vortex evaluated in accordance with "Testing method for water absorption rate of super absorbent polymers" defined in JIS K 7224 (1996).

The "gel grinding energy" in accordance with an embodiment of the present invention refers to a unit energy required for a gel-crusher to carry out gel-crushing of a hydrogel, i.e., a mechanical energy per unit mass of the hydrogel, and does not include an energy used to heat or cool a jacket or an energy of water and steam to be introduced. Note that the "gel grinding energy" is abbreviated as "GGE".

In a case where the gel-crusher is driven with three-phase alternate-current power, the GGE can be calculated according to the following formula (I):

$$\text{GGE[J/g]}=\{\sqrt{3}\times\text{voltage}\times\text{current}\times\text{power factor}\times\text{motor efficiency}\}/\{\text{mass of hydrogel introduced into gel-crusher per second}\} \qquad \text{formula (I).}$$

The "power factor" and the "motor efficiency" are values that are specific to the gel-crusher and vary depending on the operating condition(s) and/or the like of the gel-crusher, and each take a value from 0 to 1 inclusive. These values are available from the manufacturer of the gel-crusher. In a case where the gel-crusher is driven with a single-phase alternate-current power, the GGE can be calculated according to the formula (I) in which "√3" is replaced with "1". Note that the unit of voltage is [V], the unit of current is [A], and the unit of the mass of the hydrogel is [g/s].

The "power factor" and the "motor efficiency" in the GGE are the values obtained during the gel-crushing. The values of the power factor and the motor efficiency during idling operation are approximately defined as in the above-described formula (I), since a current value during idling operation is small. For example, the "mass of hydrogel introduced into gel-crusher per second" [g/s] in the formula (I) is a value converted into [g/s], in a case where the hydrogel is continuously fed with a constant feeder. Note, however, that the hydrogel may occasionally contain a recycled granular gel, as will be described later.

The gel grinding energy (GGE) for carrying out gel-crushing of the gel in accordance with an embodiment of the present invention is preferably not more than 100 J/g, more preferably not more than 80 J/g, even more preferably not more than 60 J/g, and preferably not less than 20 J/g, more preferably not less than 25 J/g, even more preferably not less than 30 J/g. Controlling the gel grinding energy so as to fall within the above-described range makes it possible to carry out gel-crushing while applying a suitable shearing force and a suitable compressive force to the hydrogel.

There may be a case where the gel-crushing is carried out with a plurality of devices, such as a case where a screw extruder is used after kneader polymerization and/or a case where a plurality of screw extruders are used. In such a case, the sum of the energies consumed by the devices is considered as the gel grinding energy (GGE).

The gel grinding energy may be controlled in the above-described manner in combination with addition of hot water of the above-described temperature. This can provide a more effective result. Furthermore, after the gel-crushing carried out in a general manner, gel-crushing in accordance with the gel grinding energy may be carried out.

The particle diameter of the particulate hydrogel obtained as a result of crushing in the gel-crushing step is preferably not less than 0.1 mm and not more than 10 mm, from the viewpoints of the ease of drying and the physical properties of the water-absorbing resin to be obtained. The mass average particle diameter (D50) of the particulate hydrogel is preferably 0.1 mm to 5.0 mm, more preferably 0.1 mm to 2.0 mm. Setting the mass average particle diameter (D50) of the particulate hydrogel so as to fall within the above range enables sufficient drying. In an embodiment of the present invention, the hydrogel that is to be subjected to the drying step preferably has a mass average particle diameter within the above-described range. More preferably, the hydrogel that is to be subjected to the drying step has a particle diameter and a mass average particle diameter both satisfying the above ranges.

A logarithmic standard deviation (σξ), which indicates narrowness of the particle size distribution of the particulate hydrogel, is preferably 0.2 to 1.5, more preferably 0.2 to 1.3, even more preferably 0.2 to 1.2. The logarithmic standard deviation (σξ) of the particle size distribution indicates the narrowness of the particle size distribution. A smaller logarithmic standard deviation indicates more uniform particle diameters, which enables uniform drying, advantageously. However, in order to set the logarithmic standard deviation (σξ) of the particle size distribution so as to be less than 0.2, it is necessary to carry out a special operation, such as classification of a particulate hydrogel after gel-crushing. Thus, from the viewpoints of the productivity and cost, it is difficult to substantially set the logarithmic standard deviation (σξ) so as to be less than 0.2. Note that the mass average particle diameter (D50) and the logarithmic standard deviation (σξ) of the particulate hydrogel are measured by the method described in WO 2021/140905, for example.

For the purpose of uniform and efficient drying, the moisture content of the particulate hydrogel is preferably not less than 30 mass %, more preferably not less than 45 mass %, and preferably not more than 70 mass %, more preferably not more than 55 mass %.

[3-4] Drying Step (Step (iv))

This step is a step of drying the hydrogel having been subjected to gel-crushing to obtain a dried polymer. Specifically, this step is a step of obtaining a dried polymer by drying the particulate hydrogel or (if a granular gel is added) both the particulate hydrogel and the granular gel until a desired solid content is obtained. The solid content, that is, a value obtained by subtracting a moisture content from 100 mass % of the gel is preferably not less than 80 mass %, more preferably not less than 85 mass %, even more preferably not less than 90 mass %, particularly preferably not less than 92 mass %, and preferably not more than 99 mass %, more preferably not more than 98 mass %, particularly preferably not more than 97 mass %. Setting the solid content of the dried polymer so as to fall within the above range makes it possible to efficiently carry out pulverization, classification, and surface-crosslinking. Note that the expression "drying is completed" herein means a state where the solid content has reached 80 mass %. In this step, the dried polymer may be in the form of a block. The block may have different moisture contents in its upper part, lower part, intermediate part, and edge parts. In such a case, pieces may be taken from various parts of the dried polymer as appropriate and may be crushed as needed. Then, moisture contents may be measured therein and the average of the moisture contents may be calculated.

Herein, a dried polymer having a solid content below a desired value may occasionally be expressed as an "undried matter". A "matter to be dried" or a "particulate hydrogel" in the drying step may occasionally include both the particulate hydrogel and the granular gel. The drying step in accordance with the embodiment of the present invention can be a condition that is more effective particularly in a case where the "matter to be dried" or the "particulate hydrogel" includes both the particulate hydrogel and the granular gel. Note that, also in the other step(s), the hydrogel and a matter obtained through a treatment(s) on the hydrogel may occasionally include the granular gel and a matter obtained through a treatment(s) on the granular gel.

Examples of a drying method employed in the drying step encompass thermal drying, hot air drying, drying under reduced pressure, fluidized bed drying, infrared drying, microwave drying, drying by azeotropic dehydration with a hydrophobic organic solvent, high humidity drying by use of high temperature water vapor, and stirring drying. Of these, the stirring drying or the hot air drying is preferable, from the viewpoint of the drying efficiency. The stirring drying is preferably carried out with a stirring drier such as a paddle dryer or a rotary-drum dryer. The hot air drying is preferably carried out with a through-flow belt-type dryer with which hot air drying is carried out on a through-flow belt. With the through-flow belt-type dryer, it is possible to carry out the drying efficiently, while preventing troubles such as physical damage of a dried polymer and/or a matter to be dried (e.g., a particulate hydrogel during drying) and/or generation of fine powder due to friction.

In consideration of the drying efficiency, a drying temperature in hot air drying, i.e., a hot air temperature is preferably not lower than 120° C., more preferably not lower than 130° C., even more preferably not lower than 150° C., and preferably not higher than 250° C., more preferably not higher than 230° C., even more preferably not higher than 200° C. A drying time is preferably 10 minutes to 120 minutes, more preferably 20 minutes to 90 minutes, even more preferably 30 minutes to 60 minutes. Setting the drying temperature and the drying time so as to fall within the above ranges yields a water-absorbing resin having physical properties within desired ranges. Note that other drying conditions may be appropriately set according to the moisture content, the total mass, and the target solid content of a particulate hydrogel and/or a granular gel to be subjected to drying. In a case where band drying is employed, the various conditions disclosed in, for example, the pamphlets of International Publication Nos. WO 2006/100300, WO 2011/025012, WO 2011/025013, and WO 2011/111657 can be applied as appropriate.

[3-5] Pulverizing Step, Classification Step (Step (v))

The pulverizing step is a step of pulverizing the dried polymer, and the classification step is a step of removing fine powder from the dried polymer having been pulverized. Specifically, the pulverizing step pulverizes the dried polymer obtained through the drying step, and the classification step adjusts the particle size of the dried polymer thus pulverized to a particle size within a desired range, so that a water-absorbing resin is obtained. By subjecting the dried polymer to the pulverizing step, it is possible to yield a water-absorbing resin having a non-uniformly pulverized shape.

Examples of a pulverizing device used in the pulverizing step encompass a high-speed rotation pulverizer (such as a roll mill, a hammer mill, a screw mill, or a pin mill), a vibration mill, a knuckle-type pulverizer, and a cylindrical mixer. Of these, the roll mill is preferably selected, from the viewpoint of the pulverizing efficiency. Two or more of these pulverizing devices may be used in combination.

Examples of the method for adjusting the particle size employed in the classification step encompass sieve classification involving use of a JIS-standard sieve (JIS Z 8801-1(2000)) and airflow classification. Of these, the sieve classification is preferably selected, from the viewpoint of the classification efficiency. Note that, from the viewpoint of the ease of pulverization, the classification step may be additionally carried out before the pulverizing step.

For particle size distribution of the water-absorbing resin, a mass average particle diameter (D50) is preferably not less than 300 μm and not more than 600 μm, and a proportion of particles of less than 150 μm is preferably not more than 5 mass %. The upper limit of the mass average particle diameter (D50) is more preferably not more than 500 μm, even more preferably not more than 450 μm. The proportion of the particles of less than 150 μm is more preferably not more than 4 mass %, even more preferably not more than 3 mass %, particularly preferably not more than 2 mass %. The logarithmic standard deviation (σξ), which indicates narrowness of the particle size distribution, is preferably not less than 0.20, more preferably not less than 0.25, even more preferably not less than 0.27, and preferably not more than 0.50, more preferably not more than 0.45, even more preferably not more than 0.43, particularly preferably not more than 0.40, most preferably not more than 0.35. The logarithmic standard deviation (σξ) of the particle size distribution indicates narrowness of the particle size distribution. Setting the logarithmic standard deviation smaller provides a more uniform particle size and less segregation of particles, advantageously. It is preferable to set the mass average particle diameter (D50) and the proportion of the particles of less than 150 μm so as to fall within the above ranges. It is more preferable to set the mass average particle diameter (D50), the proportion of the particles of less than 150 μm, and the logarithmic standard deviation so as to fall within the above ranges. The mass average particle diameter, the particles of less than 150 μm, and the logarithmic standard deviation selected within the above ranges may be combined as appropriate.

Note that the mass average particle diameter (D50) and the logarithmic standard deviation (σξ) can be measured by measurement methods described in "(3) Mass-Average Particle Diameter (D50) and Logarithmic Standard Deviation (σξ) of Particle Diameter Distribution" in U.S. Pat. No. 7,638,570.

The above-described particle size is applied also to a water-absorbing resin after the pulverizing step and the classification step. Thus, surface-crosslinking is preferably carried out in the surface-crosslinking step in such a manner as to maintain the particle size of the water-absorbing resin before surface-crosslinking having been adjusted so as to fall within the above range. More preferably, a sizing step is provided after the surface-crosslinking step so as to adjust the particle size. That is, also for a water-absorbing resin comprised by an absorbent article produced by a production method in accordance with an embodiment of the present invention, it is preferable to set the mass average particle diameter (D50) and the proportion of the particles of less than 150 μm so as to fall within the above ranges, and it is more preferable to set the mass average particle diameter (D50), the proportion of the particles of less than 150 μm, and the logarithmic standard deviation (σξ) of the particle size distribution so as to fall within the above ranges. Even more preferably, a water-absorbing resin comprised by an absorbent article produced by a production method in accordance with an embodiment of the present invention has a mass average particle diameter (D50) being 300 μm to 600 μm, a proportion of particles of less than 150 μm being not more than 5 mass %, and a logarithmic standard deviation (σξ) of a particle size distribution being 0.20 to 0.50.

[3-6] Surface-Crosslinking Step (Strep (vi))

This step is a step of providing a higher crosslinking density part in a surface layer of the water-absorbing resin before surface-crosslinking that is obtained through the above-described steps, and includes a mixing step, a heat treatment step, a cooling step, and/or the like. In the surface-crosslinking step, a reaction(s) such as radical crosslinking, surface polymerization, and a crosslinking reaction with a surface-crosslinking agent occurs in the surface of the water-absorbing resin before surface-crosslinking. Consequently, a surface-crosslinked water-absorbing resin is obtained.

A maximum temperature (powder temperature) of the water-absorbing resin in the surface-crosslinking step, i.e., a maximum temperature (powder temperature) of the water-absorbing resin in the heat treatment step is preferably not lower than 180° C., more preferably not less than 190° C.

[3-6-1] Mixing Step

This step is a step of mixing a solution containing a surface-crosslinking agent (hereinafter, referred to as a "surface-crosslinking agent solution") with the water-absorbing resin before surface-crosslinking in a mixing device to obtain a mixture.

(Surface-Crosslinking Agent)

In an embodiment of the present invention, a surface-crosslinking agent is used in surface-crosslinking. The surface-crosslinking agent is as described in "[Polyacrylic acid (salt)-based water-absorbing resin]" above.

The used amount of the surface-crosslinking agent (if plural kinds of surface-crosslinking agents are used, the total amount thereof) is preferably 0.01 parts by mass to 10.00 parts by mass, more preferably 0.01 parts by mass to 5.00 parts by mass, even more preferably 0.01 parts by mass to 2.00 parts by mass, relative to 100 parts by mass of the crosslinked polymer. Setting the used amount of the surface-crosslinking agent so as to fall within the above range makes it possible to form an optimum crosslinking structure in the surface layer of the crosslinked polymer. Consequently, the water-absorbing resin having excellent physical properties can be obtained.

The surface-crosslinking agent added to the water-absorbing resin before surface-crosslinking is preferably in the form of an aqueous solution. In this case, the amount of water to be used is preferably 0.1 parts by mass to 20.0 parts by mass, more preferably 0.3 parts by mass to 15.0 parts by mass, even more preferably 0.5 parts by mass to 10 parts by mass, relative to 100 parts by mass of the water-absorbing resin before surface-crosslinking. Setting the used amount of the water so as to fall within the above range improves the ease of the handling of the surface-crosslinking agent solution, thereby making it possible to uniformly mixing the surface-crosslinking agent with the water-absorbing resin before surface-crosslinking.

In addition, a hydrophilic organic solvent may be used in combination with water, as needed, so as to obtain the surface-crosslinking agent solution. In this case, the amount of the hydrophilic organic solvent to be used is preferably not more than 5 parts by mass, more preferably not more than 3 parts by mass, even more preferably not more than 1 part by mass, relative to 100 parts by mass of the water-absorbing resin before surface-crosslinking. Specific examples of the hydrophilic organic solvent encompass: lower alcohols such as methyl alcohol; ketones such as acetone; ethers such as dioxane; amides such as N,N-dimethylformamide; sulfoxides such as dimethylsulfoxide; and polyhydric alcohols such as ethylene glycol. However, the amount of the hydrophilic organic solvent to be used is preferably as small as possible.

In addition, various kinds of additives may be added to the surface-crosslinking agent solution or may be added in the mixing step, in an amount of not more than 5 parts by mass.

(Mixing Method and Mixing Conditions)

Mixing of the water-absorbing resin and the surface-crosslinking agent solution may be carried out by a method of spraying or dripping a preliminarily prepared surface-crosslinking agent solution to a crosslinked polymer, preferably, spraying the preliminarily prepared surface-crosslinking agent solution to the crosslinked polymer.

The mixing device used for the mixing preferably has a torque required to uniformly and reliably mix the water-absorbing resin and the surface-crosslinking agent. The mixing device is preferably a high-speed stirring mixer, more preferably a high-speed stirring continuous mixer. The number of revolutions of the high-speed stirring mixer is preferably not less than 100 rpm, more preferably not less than 300 rpm, and preferably not more than 10000 rpm, more preferably not more than 2000 rpm.

The temperature of the water-absorbing resin to be supplied in this step is preferably 35° C. to 80° C., more preferably 35° C. to 70° C., even more preferably 35° C. to 60° C., from the viewpoints of the miscibility with the surface-crosslinking agent solution and/or the agreeability of the moistened mixture. The mixing time is preferably not less than one second, more preferably not less than five seconds, and preferably not more than one hour, more preferably not more than 10 minutes.

[3-6-2] Heat Treatment Step

This step is a step of heating the mixture obtained in the mixing step, so as to cause a crosslinking reaction on the surface of the water-absorbing resin. The heat treatment of the water-absorbing resin may be carried out by heating the water-absorbing resin left at rest or by heating the water-absorbing resin that is caused to flow by stirring power and/or the like. Preferably, the water-absorbing resin is heated while the water-absorbing resin is being stirred, since this can uniformly heat the entire moistened mixture. From this viewpoint, used as a heat treatment device for the heat treatment may be, for example, a paddle dryer, a multi-fin processor, or a tower dryer.

A so-called control temperature of the heat treatment device only needs to be set so that the water-absorbing resin can be heated to the later-described temperature, and does not need to be constant from the beginning to the end of this step. However, in order to prevent a trouble such as partial overheating, the control temperature is preferably 50° C. to 300° C. In a case where damage resistance is particularly important among the physical properties of the water-absorbing resin to be obtained, the control temperature is more preferably not higher than 250° C., more preferably 70° C. to 230° C., even more preferably 90° C. to 220° C.

Meanwhile, in a case where the water absorption performance is particularly important, the control temperature is more preferably 120° C. to 280° C., even more preferably 150° C. to 250° C., and particularly preferably 170° C. to 230° C.

The heating time is preferably 1 minute to 180 minutes, more preferably 5 minutes to 120 minutes, even more preferably 10 minutes to 120 minutes, still more preferably 15 minutes to 60 minutes. Setting the heating time so as to be less than 1 minute may result in an insufficient surface-crosslinking treatment, thereby reducing the absorption against pressure (AAP). Meanwhile, setting the heating time long may result in coloration of the water-absorbing resin and/or may reduce the centrifuge retention capacity (CRC) of the water-absorbing resin too much.

[3-6-3] Cooling Step

This step is an optional step provided as needed after the heat treatment step and/or the drying step. This step is a step of forcibly cooling the high-temperature water-absorbing resin after the heat treatment step to a given temperature to quickly stop the surface-crosslinking reaction.

The cooling may be carried out by cooling the water-absorbing resin left at rest or by cooling the water-absorbing resin that is caused to flow by stirring power and/or the like. Preferably, the water-absorbing resin is cooled while the water-absorbing resin is being stirred, since this can uniformly cool the entire water-absorbing resin. From this viewpoint, used as a cooling device for the cooling may be, for example, a paddle dryer, a multi-fin processor, or a tower dryer. Note that the cooling device may be the one having the same specification as that of the heat treatment device used in the heat treatment step. The heat treatment device in which a heating medium is replaced with a refrigerant can be used as the cooling device.

The cooling temperature in this step may be appropriately set according to the heating temperature in the heat treatment step, the water absorption performance of the water-absorbing resin, and/or the like, and is preferably 40° C. to 100° C., more preferably 50° C. to 90° C., even more preferably 50° C. to 70° C.

[4] Absorbent Articles

A water-absorbing resin produced by a production method in accordance with an embodiment of the present invention is incorporated in absorbent articles. "Absorbent articles" refers to products that are placed against or in proximity to the body of the wearer to absorb and contain the various exudates discharged from the body, such as urine, fecal matter, blood and the like. Absorbent articles include paper diapers and pants (to be worn by babies, infants and/or adults), absorbent inserts for paper diapers or pants, feminine care absorbent articles such as sanitary napkins and pantiliners, and the like.

Absorbent articles may each include a topsheet, a backsheet, an absorbent core and optionally an acquisition-distribution system. The absorbent core is placed between the backsheet and the topsheet, the optional acquisition-distribution system is typically placed between the absorbent core and the topsheet.

A water-absorbing resin produced by a production method in accordance with an embodiment of the present invention may be incorporated in the absorbent core of the absorbent article. The absorbent core may or may not include other absorbent material, such as non-crosslinked cellulose fibers (pulp fibers). The absorbent core may include at least 60 mass %, at least 75 mass %, at least 85 mass %, at least 95 mass %, or at least 98 mass %, or 100 mass % of a water-absorbing resin, such as the water-absorbing resin disclosed herein.

The "paper diaper" and "pant" each refer to an absorbent article that is to be worn by babies, infants and incontinent (adult) persons about the lower torso so as to encircle the waist and legs of the wearer and that is specifically adapted to receive and contain urine and fecal waste. In a pant, as used herein, the longitudinal edges of first and second waist regions of the pant are attached to each other to pre-form a waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be pre-formed anywhere along the circumference of the article (e.g., side fastened, front waist fastened). In a paper diaper, the waist opening and leg openings are only formed when the paper diaper is applied onto a wearer by (releasably) attaching the longitudinal edges of first and second waist regions of the paper diaper to each other on both sides of the wearer with a suitable fastening system. The suitable fastening system may include, e.g., tape tabs including a hook material and a landing zone cooperating therewith (e.g., a nonwoven web providing loops in a hook and loop fastening system).

A paper diaper or pant may also include elasticized leg cuffs and barrier leg cuffs, which provide improved containment of liquids and other body exudates especially in the area of the leg openings. Usually each of the leg cuffs and barrier cuffs includes one or more elastic strings.

A "feminine care absorbent article" is a personal care product used by women during menstruation to absorb and retain menses, vaginal discharge, and matters from other bodily functions related to vulva. Feminine care absorbent articles include pantiliners and sanitary napkins.

The present invention can include the following [1] to [8]:

[1] An absorbent article comprising poly(meth)acrylic acid (salt)-based water-absorbing resin in particulate form, the water-absorbing resin including:

water-soluble polyalkylene glycol having a weight average molecular weight of not more than 2000, the polyalkylene glycol being contained in the water-absorbing resin, the water-absorbing resin substantially not including a liquid permeability enhancer including a polyvalent metal salt and/or water-insoluble inorganic particles, the water-absorbing resin satisfying (1) to (5) below:

(1) a centrifuge retention capacity (CRC) of not less than 20 g/g and not more than 35 g/g;

(2) an absorption against pressure (AAP), measured under a load of 0.7 psi, of not less than 25 g/g;

(3) a saline flow conductivity (SFC) of not less than 15 (×10-7 cm3·sec/g);

(4) a free swell rate (FSR) of not less than 0.33 g/(g s); and (5) an initial water absorption speed under load (T20) of not more than 145 seconds.

[2] The absorbent article described in [1], wherein the polyalkylene glycol has a weight average molecular weight of not less than 200.

[3] The absorbent article described in [1] or [2], wherein a content of the polyalkylene glycol is 0.01 mass % to 1 mass %, relative to the entire water-absorbing resin.

[4] The absorbent article described in any one of [1] to [3], wherein the water-absorbing resin is a surface-crosslinked water-absorbing resin having a non-uniformly pulverized shape.

[5] The absorbent article described in any one of [1] to [4], wherein the water-absorbing resin has an initial water absorption speed under load (T5) of not more than 25 seconds.

[6] The absorbent article described in any one of [1] to [5], wherein, for the water-absorbing resin, a sum of T5, T10, and T15, each of which is an initial water absorption speed under load, is not more than 160 seconds.

[7] The absorbent article described in any one of [1] to [6], wherein the water-absorbing resin has a moisture content of not more than 5 mass %.

[8] A method for producing an absorbent article comprising a poly(meth)acrylic acid (salt)-based water-absorbing resin in particulate form, the method including the steps of:

(i) preparing a (meth)acrylic acid (salt)-based aqueous monomer solution;

(ii) polymerizing the (meth)acrylic acid (salt)-based aqueous monomer solution;

(iii) carrying out gel-crushing of a crosslinked hydrogel polymer generated during or after the polymerization to obtain a hydrogel in particulate form;

(iv) drying the hydrogel in particulate form to obtain a dried polymer;

(v) pulverizing and/or classifying the dried polymer to obtain a water-absorbing resin in particulate form;

(vi) surface-crosslinking the water-absorbing resin in particulate form; and (vii) incorporating the surface-crosslinked particulate water-absorbing resin in an absorbent article, wherein in any of the steps prior to the step (iii), water-soluble polyalkylene glycol having a weight average molecular weight of not more than 2000 is added in an amount of 0.01 mass % to 1 mass % relative to a total mass of a monomer included in the aqueous monomer solution, a liquid permeability enhancer including a polyvalent metal salt and/or water-insoluble inorganic particles is not substantially added in any of the steps, and the water-absorbing resin obtained satisfies (1) to (5) below:

(1) a centrifuge retention capacity (CRC) of not less than 20 g/g and not more than 35 g/g;

(2) an absorption against pressure (AAP), measured under a load of 0.7 psi, of not less than 25 g/g;

(3) a saline flow conductivity (SFC) of not less than 15 (×10-7 cm3·sec/g);

(4) a free swell rate (FSR) of not less than 0.33 g/(g s); and (5) an initial water absorption speed under load (T20) of not more than 145 seconds.

EXAMPLES

The following description will discuss the water-absorbing resin comprised by the absorbent article of the present invention according to Examples and Comparative Examples. However, it will be understood that the present invention is not limited to these Examples and Comparative Examples. The physical properties described in the claims and Examples of the present invention were calculated under the conditions of room temperature (23±2° C.) and a humidity of 50±10RH %.

[Measurement and Evaluation of Physical Properties of Water-Absorbing Resin]

The physical properties and the like of the water-absorbing resins obtained in the following Examples and Comparative Examples were measured and evaluated in the following manner.

(Absorption Capacity without Pressure (CRC))

The CRC of the water-absorbing resin was measured in accordance with NWSP 241.0.R2 (15). Specifically, 0.2 g of the water-absorbing resin was added to a nonwoven fabric bag. The bag was then immersed in a large excess of a 0.9 mass % aqueous sodium chloride solution for 30 minutes so as to be swollen freely. The bag was drained with a centrifuge (250 G) for three minutes. Thereafter, a centrifuge retention capacity (CRC) (unit: g/g) thereof was measured.

(Absorption Against Pressure (AAP))

The AAP of the water-absorbing resin was measured in accordance with NWSP 242.0.R2 (15). Note that the measurement herein was carried out under a changed pressure condition, specifically, under a pressure of 4.83 kPa (49 g/cm2, 0.7 psi). To be more specific, 0.9 g of the water-absorbing resin was swollen in a large excess of a 0.9 mass % aqueous sodium chloride solution for one hour under a pressure of 4.83 kPa (49 g/cm2, 0.7 psi). Thereafter, an AAP (absorption against pressure) (unit: g/g) thereof was measured. That is, all the AAPs (absorption against pressure) herein are values measured under a pressure of 4.83 kPa.

(Centrifuge Retention Capacity of Crosslinked Hydrogel Polymer: Gel CRC)

The same operations as those carried out in the measurement of the CRC of the water-absorbing resin were carried out except that 0.6 g of a crosslinked hydrogel polymer was used as a sample and the free swelling period was set to 24 hours. Further, a resin solid content in the crosslinked hydrogel polymer was measured by the later-described method carried out additionally. The weight of the water-absorbing resin contained in 0.6 g of the crosslinked hydrogel polymer was obtained, and a gel CRC was calculated according to the following formula (2). For a single sample, the measurement was carried out five times, and an average thereof was adopted.

$$\text{Gel CRC(g/g)}=[\{(mwi-mb)/msi\}-1]\times(100/Wn) \quad \text{formula (2).}$$

In the formula (2), msi: Weight (g) of crosslinked hydrogel polymer before measurement;

mb: Weight (g) of blank (only nonwoven fabric) having been freely swollen and drained;

mwi: Total weight (g) of crosslinked hydrogel polymer and nonwoven fabric having been freely swollen and drained; and Wn: Solid content (wt %) of crosslinked hydrogel polymer.

(Resin Solid Content in Crosslinked Hydrogel Polymer)

The weight of an aluminum cup having a bottom surface having a diameter of approximately 50 mm was measured in advance, and the weight thus obtained was regarded as "Wa(g)". 1.00 (g) of the crosslinked hydrogel polymer was weighed and put into the aluminum cup, and the total weight Wb(g) of the crosslinked hydrogel polymer and the aluminum cup was measured. Then, the aluminum cup containing the water-absorbing resin was left stand for three hours in an oven having an atmospheric temperature of 180° C. for drying. After three hours, the water-absorbing resin and the aluminum cup were taken out from the oven, and were cooled down to room temperature in a desiccator. Then, the total weight Wc(g) of the water-absorbing resin and the aluminum cup after drying was measured. With use of Wa, Wb, and Wc, a resin solid content of the crosslinked hydrogel polymer was obtained according to the following formula (3):

$$\text{Resin solid content (wt \%)in crosslinked hydrogel polymer}=\{(Wc-Wa)/(Wb-Wa)\}\times 100 \quad \text{formula (3).}$$

(Saline Flow Conductivity (SFC))

The saline flow conductivity (SFC) (unit: ×10-7 cm3·sec/g) of the water-absorbing resin was measured in accordance with the measurement method described in U.S. Pat. No. 5,669,894.

Specifically, 1.500 g of the water-absorbing resin was evenly put into a container. Then, the water-absorbing resin was immersed in artificial urine so as to be swollen under a pressure of 2.07 kPa. The artificial urine was prepared by mixing 0.25 g of calcium chloride 2-hydrate, 2.0 g of potassium chloride, 0.50 g of magnesium chloride 6-hydrate, 2.0 g of sodium sulfate, 0.85 g of ammonium dihydrogen phosphate, 0.15 g of diammonium hydrogen phosphate, and 994.25 g of pure water.

After 60 minutes had elapsed since start of the pressurization, the height (cm) of a gel layer, which is the swollen water-absorbing resin, was recorded. Next, while the gel layer is pressurized with a pressure of 2.07 kPa, a 0.69 mass % saline solution was caused to pass through the gel layer. The room temperature during this process was adjusted at 20° C. to 25° C. Then, the amount of the saline solution passing through the gel layer was recorded at intervals of 20 seconds with use of a scale balance and a computer, so that the flow rate Fs(T) of the saline solution passing therethrough was measured. The flow rate Fs(T) can be obtained by dividing, by the passing time (s), the mass (g) of the passing saline solution that increases every 20 seconds. Here, it is assumed that Ts represents the time when the hydrostatic pressure of the saline solution became constant and a stable flow rate could be obtained. Then, based on the data measured for 10 minutes from Ts, a flow rate Fs(T=0) was calculated. Specifically, Fs(T=0) was calculated based on the result obtained by plotting Fs(T) against the time and applying the least-squares method thereto. Fs(T=0) is a flow rate (g/s) of a first flow of the saline solution passing through the gel layer. Then, the saline flow conductivity (SFC) was calculated according to the following formula (4).

$$SFC=\{Fs(T=0)\times L0\}/(\rho\times A\times\Delta P) \quad \text{formula (4).}$$

In the formula (4), L0 is the height (cm) of the gel layer, p is the density (g/cm3) of the saline solution, A is the cross-sectional area A (cm2) of the gel layer, and ΔP is the hydrostatic pressure (dyne/cm2) applied to the gel layer.

(Free Swell Rate (FSR))

The free swell rate (FSR) is the rate (g/(g s)) at which 1 g of the water-absorbing resin absorbs 20 g of a 0.9 mass % aqueous sodium chloride solution, and was measured according to the method described in International Publication No. WO 2009/016055.

(Moisture Content)

1.00 (g) of the water-absorbing resin was weighed out, and was put into an aluminum cup having a bottom surface with a diameter of approximately 50 mm. Then, the total mass W1(g) of the water-absorbing resin and the aluminum cup was measured. Thereafter, the aluminum cup containing the water-absorbing resin was left at rest in an oven of an atmosphere temperature of 180° C. for three hours so as to be dried. After three hours had elapsed, the water-absorbing resin and the aluminum cup were taken out from the oven, and were cooled to room temperature in a desiccator. Thereafter, the total mass W2(g) of the water-absorbing resin and the aluminum cup after drying was measured, and the moisture content was obtained according to the following formula:

$$\text{Moisture content(mass \%)}=(W1-W2)/(\text{mass(g) of water-absorbing resin})\times 100.$$

(T20, T5, T10, T15)

T20 was measured as a period of time (seconds) required for 1 g of the water-absorbing resin to absorb 20 g of an aqueous solution prepared by dissolving 9 g of sodium chloride and 0.1 g of Lorodac (main component: a C12-14 liner alcohol ethoxylate, CAS No. 68439-50-9) in 1 L of distilled water. Specifically, T20 was measured in accordance with the measurement method described in Japanese Translation of PCT International Application Publication No. 2014-515987. Similarly, T5, T10, and T15 were periods of time required for 1 g of the water-absorbing resin to absorb 5 g, 10 g, and 15 g of the aqueous solution, respectively. Similarly to T20, T5, T10, and T15 were measured in accordance with the measurement method described in Japanese Translation of PCT International Application Publication No. 2014-515987.

(EFFC)

The EFFC is the average of the centrifuge retention capacity (CRC) and the absorption against pressure (AAP).

Example 1

(Preparation of (Meth)Acrylic Acid (Salt)-Based Aqueous Monomer Solution)

There was prepared an aqueous solution (1) by introducing, into a propylene container having a capacity of 2 L, 400 parts by mass of acrylic acid, 185 parts by mass of a 48 mass % aqueous sodium hydroxide solution, 2.5 parts by mass of polyethylene glycol diacrylate (PEGDA, an average addition mole number of ethylene oxide: 9), 1.3 parts by mass of a 2 mass % aqueous trisodium diethylenetriamine pentaacetate solution, 373 parts by mass of deionized water, and 0.9 parts by mass (0.225 mass % relative to the acrylic acid) of polyethylene glycol (PEG) 600 (weight average molecular weight: 600, available from FUJIFILM Wako Pure Chemical Corporation) and by mixing them. The aqueous solution (1) was heated to 40° C. in advance.

Next, while the heated aqueous solution (1) was being stirred, 185 parts by mass of a 48 mass % aqueous sodium hydroxide solution was introduced into the aqueous solution (1) in an air open state by taking approximately 30 seconds, and then these solutions were mixed. In this manner, an aqueous monomer solution was prepared. Note that the temperature of the aqueous monomer solution was increased to approximately 84° C. by the heat of neutralization and the heat of solution generated in the mixing process.

Table 1 below shows the weight average molecular weights of PEGs, the added amounts of PEGs (mass % relative to the acrylic acid), and the added amounts of PEGDAs (mass % relative to the acrylic acid).

(Polymerization of (Meth)Acrylic Acid (Salt)-Based Monomer)

At a timing when the temperature of the aqueous monomer solution reached 83° C., 13 parts by mass of a 5 mass % aqueous sodium persulfate solution was added as a polymerization initiator to the aqueous monomer solution, and a resulting mixture was stirred for approximately five seconds. Consequently, a reaction liquid (1) was obtained.

Next, the reaction liquid (1) was poured into a stainless-steel tray-type container (with a bottom surface of 340 mm×340 mm, a height of 25 mm, and an inner surface attached with Teflon (registered trademark)) in an open air state. Note that the tray-type container was preliminarily heated with a hot plate so that a surface temperature thereof became 40° C.

Within one minute after the reaction liquid (1) was poured into the tray-type container, polymerization reaction started. As a result of the polymerization reaction, the reaction liquid (1) expanded and foamed upward in all directions while generating water vapor. As a result of the polymerization reaction proceeded in this manner, a reactant shrank to a size slightly larger than the bottom surface of the tray-type container. The polymerization reaction ended in approximately one minute. As a result of the polymerization reaction, a crosslinked hydrogel polymer was obtained. A portion of the crosslinked hydrogel polymer was cut out, and the portion was used as a sample for measurement. The sample for measurement was used for measurement of gel CRC. The obtained value of the gel CRC of the crosslinked hydrogel polymer is shown in Table 1.

(Gel-Crushing)

Next, the remaining portion of the crosslinked hydrogel polymer which had not been used for the measurement of the gel CRC was cut into pieces of a suitable size, and the pieces of the crosslinked hydrogel polymer were subjected to gel-crushing by a meat chopper (model number: "HL-G22SN", available from Remacom Co. Ltd.) with a die having 33 holes each having a diameter of 8 mm, so that a particulate hydrogel was obtained. The particulate hydrogel had a mass average particle diameter of 400 μm.

(Drying, Pulverization, Classification)

The particulate hydrogel was spread over a metal mesh of 50-mesh (mesh size: 300 μm), and was subjected to hot air drying at 180° C. for 30 minutes by use of a ventilation batch-type dryer (model type: "71-S6", Satake Chemical Equipment Mfg. Ltd.). Consequently, a dried polymer was obtained. Next, the dried polymer was subjected to the pulverizing step involving use of a roll mill, and a resulting pulverized matter was subjected to classification with a metal mesh having a mesh size of 710 μm and a metal mesh having a mesh size of 150 μm. Consequently, (particulate) crosslinked polymer powder having a non-uniformly pulverized shape and a particle diameter of 150 μm to 710 μm was obtained. The crosslinked polymer powder thus obtained corresponds to the water-absorbing resin before surface-crosslinking.

(Surface-Crosslinking)

To 100 parts by mass of the crosslinked polymer powder thus obtained, (4.0 parts by mass of) an aqueous surface-crosslinking agent solution including 0.4 parts by mass of ethylene carbonate, 0.7 parts by mass of propylene glycol, and 2.9 parts by mass of deionized water was mixed by spraying. A resulting mixture was subjected to a heat treatment involving use of a mixer at a heating medium temperature of 210° C. for 40 minutes. Then, the mixture was pulverized into a size with which the mixture could pass through a JIS-standard sieve having a mesh size of 710 μm. In this manner, a surface-crosslinked water-absorbing resin was obtained. The physical properties of the water-absorbing resin thus obtained are shown in Table 1 below.

Examples 2 to 7

The same procedures as those of Example 1 were carried out, except that the weight average molecular weights and the added amounts of PEGs were changed to the values shown in Table 1. As a result, water-absorbing resins of Examples 2 to 7 were obtained. The physical properties of the water-absorbing resins thus obtained are shown in Table 1. In Table 1, the weight average molecular weight of PEG200 (available from FUJIFILM Wako Pure Chemical Corporation) was 200, and the weight average molecular weight of PEG2000 (available from FUJIFILM Wako Pure Chemical Corporation) was 2000.

Example 8

The same procedures as those of Example 1 were carried out, except that (i) the weight average molecular weight and the added amount of PEG were changed to the values shown in Table 1, (ii) the die used in the gel-crushing step was changed to a die having 52 holes each having a diameter of 6 mm, and (iii) an aqueous surface-crosslinking agent solution (3.08 parts by mass) including 0.18 parts by mass of 1,6-hexanediol, 0.4 parts by mass of triethylene glycol, and 2.5 parts by mass of deionized water was applied to 100 parts by mass of a crosslinked polymer powder obtained in the surface-crosslinking step. As a result, a water-absorbing resin of Example 8 was obtained.

Example 9

The same procedures as those of Example 1 were carried out, except that (i) the weight average molecular weight and the added amount of PEG were changed to the values shown in Table 1, (ii) the die used in the gel-crushing step was changed to a die having 52 holes each having a diameter of 6 mm, and (iii) an aqueous surface-crosslinking agent solution (3.30 parts by mass) including 0.67 parts by mass of ethylene carbonate and 2.63 parts by mass of deionized water was applied to 100 parts by mass of a crosslinked polymer powder obtained in the surface-crosslinking step. As a result, a water-absorbing resin of Example 9 was obtained.

Example 10

The same procedures as those of Example 1 were carried out, except that (i) the weight average molecular weight and the added amount of PEG were changed to the values shown in Table 1, (ii) the die used in the gel-crushing step was changed to a die having 52 holes each having a diameter of 6 mm, and (iii) an aqueous surface-crosslinking agent solution (3.0 parts by mass) including 1.0 part by mass of triethylene glycol and 2.0 parts by mass of deionized water was applied to 100 parts by mass of a crosslinked polymer powder obtained in the surface-crosslinking step. As a result, a water-absorbing resin of Example 10 was obtained.

Comparative Example 1

The same procedures as those of Example 1 were carried out, except that PEG was not added in Comparative Example 1. As a result, a water-absorbing resin of Comparative Example 1 was obtained. The physical properties of the water-absorbing resin thus obtained are shown in Table 1.

Comparative Examples 2 and 3

The same procedures as those of Example 1 were carried out, except that the added amounts of PEGs were changed to the values shown in Table 1 and the heating conditions were adjusted so that the SFCs as shown in Table 1 were obtained in the surface-crosslinking step. As a result, water-absorbing resins of Comparative Examples 2 and 3 were obtained. The physical properties of the water-absorbing resins thus obtained are shown in Table 1.

Comparative Example 4

To a reaction container consisting of a thermometer, a lid provided with a nitrogen-gas introduction tube and an exhaust hole, and a tray having a bottom surface of 300 mm×220 mm and a depth of 60 mm, 170 g of acrylic acid, 1800 g of a 37 mass % aqueous sodium acrylate solution, 0.99 g of polyethylene glycol diacrylate (weight average molecular weight: 523), 6.688 g (0.8 mass % relative to the acrylic acid) of PEG2000 (weight average molecular weight: 2000, available from FUJIFILM Wako Pure Chemical Corporation), and 216 g of deionized water were introduced and mixed. Then, the reaction container was immersed in a water bath at 20° C. A nitrogen gas was introduced into the aqueous solution, and the aqueous solution was degassed for 20 minutes.

After confirming that the temperature of the solution reached 20° C., 6.61 g of a 20 mass % aqueous sodium persulfate solution and 6.33 g of a 0.1 mass % aqueous L-ascorbic acid solution were added thereto in a flowing nitrogen atmosphere, and a resultant was stirred for mixing. The concentration of the monomer was 38 mass %.

After one minute had elapsed, polymerization started. The temperature of the reaction system at that time was 20° C. After the polymerization was initiated, the reaction container was cooled by being immersed in the water bath at 20° C., without stirring the polymerization system. After 17 minutes, the polymerization system exhibited a temperature of 89° C., which was the maximum temperature. Thereafter, the temperature of the water bath was increased to 70° C., and the polymerization reaction was carried out for 20 minutes, so that a crosslinked hydrogel polymer was obtained. A portion of the crosslinked hydrogel polymer was cut out, and the portion was used as a sample for measurement. The sample for measurement was used for measurement of gel CRC. The obtained value of the gel CRC of the crosslinked hydrogel polymer is shown in Table 1.

The remaining portion of the obtained crosslinked hydrogel polymer which had not been used for the measurement of the gel CRC was cut into blocks, and the block-shaped pieces of the crosslinked hydrogel polymer obtained by the cutting were then subjected to gel-crushing involving use of a meat chopper provided with a 9.0-mm diameter die plate, so that a particulate hydrogel polymer was obtained.

The particulate hydrogel polymer thus obtained was dried by a hot air dryer at 180° C. for 30 minutes, so that a dried polymer was obtained. The dried polymer was then pulverized with a roll mill and subjected to classification with a metal mesh having a mesh size of 850 μm and a metal mesh having a mesh size of 150 μm. As a result, a particulate crosslinked polymer powder was obtained. The crosslinked polymer powder thus obtained corresponds to the water-absorbing resin before surface-crosslinking.

To 100 parts by mass of the crosslinked polymer powder, a surface-crosslinking agent solution including 0.025 parts by mass of ethylene glycol diglycidyl ether, 0.3 parts by mass of ethylene carbonate, 0.5 parts by mass of propylene glycol, and 2.0 parts by mass of deionized water was sprayed and a resultant was mixed. A resulting mixture was heated at 200° C. for 35 minutes, so that a surface-crosslinked particulate water-absorbing resin was obtained.

In 100 parts by mass of the surface-crosslinked water-absorbing resin, 0.6 parts by mass of fumed silica (AEROSIL 200, available from Nippon Aerosil Co. Ltd.) was mixed. As a result, a water-absorbing resin of Comparative Example 4 was obtained. The physical properties of the water-absorbing resin thus obtained are shown in Table 1.

Comparative Examples 5 and 6

The same procedures as those of Example 1 were carried out, except that the weight average molecular weights and the added amounts of PEGs were changed to the values shown in Table 1. As a result, water-absorbing resins of Comparative Examples 5 and 6 were obtained. The physical properties of the water-absorbing resins thus obtained are shown in Table 1. In Table 1, the weight average molecular weight of PEG6000 (available from Kishida Chemical Co., Ltd.) was 7300 to 9300, and the weight average molecular weight of PEG20000 (available from Kishida Chemical Co., Ltd.) was 18000 to 25000.

TABLE 1

| | Gel CRC (g/g) | PEG | Added Amount of PEG (mass %)*1 | CRC (g/g) | AAP (g/g) | EFFC | SFC*2 | FSR (g/(g · s)) | T20 (sec.) | T15 (sec.) | T10 (sec.) | T5 (sec.) | T5 + T10 + T15 (sec.) | Moisture Content (mass %) |
|---|---|---|---|---|---|---|---|---|---|---|---|---|---|---|
| Ex. 1*3 | 26.8 | PEG600 | 0.225 | 29.9 | 26.1 | 28.0 | 29 | 0.43 | 122 | 70 | 39 | 18 | 127 | 1.6 |
| Ex. 2*3 | 28.7 | PEG600 | 0.05 | 29.2 | 25.9 | 27.5 | 35 | 0.36 | 143 | 84 | 49 | 24 | 156 | 1.6 |
| Ex. 3*3 | 29.7 | PEG600 | 0.1 | 29.6 | 26.3 | 27.9 | 31 | 0.37 | 141 | 83 | 48 | 24 | 154 | 1.6 |
| Ex. 4*3 | 30.0 | PEG600 | 0.5 | 28.6 | 25.8 | 27.2 | 36 | 0.40 | 126 | 71 | 41 | 20 | 131 | 1.5 |
| Ex. 5*3 | 29.0 | PEG600 | 1 | 29.7 | 25.8 | 27.7 | 23 | 0.40 | 137 | 76 | 43 | 21 | 139 | 1.7 |
| Ex. 6*3 | 29.5 | PEG200 | 0.5 | 27.0 | 25.1 | 26.1 | 44 | 0.37 | 144 | 86 | 50 | 24 | 160 | 2.0 |
| Ex. 7*3 | 29.7 | PEG2000 | 0.5 | 29.6 | 25.9 | 27.7 | 29 | 0.37 | 136 | 78 | 46 | 22 | 145 | 1.6 |
| Ex. 8*3 | 29.3 | PEG600 | 0.225 | 28.9 | 26.5 | 27.7 | 37 | 0.49 | 101 | 61 | 36 | 19 | 115 | 1.6 |
| Ex. 9*3 | 29.5 | PEG2000 | 0.5 | 28.2 | 25.5 | 26.9 | 50 | 0.48 | 97 | 57 | 33 | 16 | 105 | 1.6 |
| Ex. 10*3 | 29.5 | PEG2000 | 0.5 | 28.3 | 25.6 | 26.9 | 39 | 0.46 | 102 | 60 | 35 | 17 | 111 | 1.6 |
| C. Ex. 1*4 | 28.5 | — | 0 | 30.2 | 26.6 | 28.4 | 29 | 0.33 | 157 | 94 | 54 | 28 | 176 | 1.6 |
| C. Ex. 2*4 | 26.8 | PEG600 | 0.225 | 32.8 | 22.6 | 27.7 | 2 | 0.41 | 220 | 122 | 64 | 26 | 212 | 2.2 |
| C. Ex. 3*4 | 29.0 | PEG600 | 1 | 31.7 | 25.3 | 28.5 | 4 | 0.45 | 160 | 90 | 49 | 23 | 162 | 2.0 |
| C. Ex. 4*4 | 32.9 | PEG2000 | 0.8 | 35 | 23.5 | 29.3 | 5 | 0.29 | 263 | 162 | 92 | 45 | 299 | 3.6 |
| C. Ex. 5*4 | 33.0 | PEG6000 | 0.225 | 28.9 | 23.5 | 26.2 | 33 | 0.24 | 194 | 113 | 64 | 31 | 208 | 1.6 |
| C. Ex. 6*4 | 29.1 | PEG20000 | 0.225 | 28.9 | 25.1 | 27.0 | 44 | 0.28 | 167 | 96 | 54 | 26 | 175 | 1.6 |

*1The concentration relative to the total mass of the monomers contained in the aqueous monomer solution.

*2($\times 10^{-7}$ $cm^3 \cdot sec/g$)

*3"Ex." stands for "Example".

*4"C. Ex." stands for "Comparative Example".

According to Table 1, the water-absorbing resins of Examples 1 to 10, each of which contained PEG, had smaller T20s, as compared to the water-absorbing resin of Comparative Example 1, which did not contain PEG. According to Table 1, as compared to the water-absorbing resins of Comparative Examples 2 and 3, each of which contained PEG but had a low SFC, the water-absorbing resins of Examples 1 and 5, each of which had the same amount of PEG as those of Comparative Examples 2 and 3 but had an SFC not less than 15 (×10-7 cm3·sec/g), had smaller T20s. In each of the water-absorbing resins of Examples 1 to 7, the CRC, AAP, EFFC, and FSR were favorable, the SFC was as high as not less than 15, and the T20, T15, T10, and T5 were reduced. The water-absorbing resin of Comparative Example 4, which had the PEG whose weight average molecular weight was equal to that of the water-absorbing resin of Example 7, exhibited an FSR of less than 0.33 (g/(g s)) and a higher T20.

As discussed above, a water-absorbing resin indicated in the present invention has favorable performance such as the absorption capacity (CRC, AAP), the water absorption speed (FSR), and the liquid permeability (SFC). In addition, the water-absorbing resin has, e.g., a small T20 value, that is, has an excellent initial water absorption speed under load. Thus, in a case where the water-absorbing resin indicated in the present invention is incorporated into an absorbent article, such as a paper diaper, the absorbent article can suppress or reduce exuding (re-wet) of urine. Therefore, it is expected that a user who wears such an absorbent article can enjoy a comfortable feeling without a stuffy feeling.

The absorbent article comprising the water-absorbing resin described above can suppress or reduce exuding (re-wet) of a discharged liquid. Thus, the water-absorbing resin indicated in the present invention can be incorporated into various kinds of absorbent articles. Therefore, a user who wears an absorbent article (e.g., a paper diaper) including the water-absorbing resin indicated in the present invention can enjoy a comfortable feeling without a stuffy feeling.

What is claimed is:

1. A method for producing an absorbent article comprising a surface-crosslinked particulate poly(meth)acrylic acid (salt)-based water-absorbing resin, said method comprising the steps of:

(i) preparing a (meth)acrylic acid (salt)-based aqueous monomer solution;

(ii) polymerizing the (meth)acrylic acid (salt)-based aqueous monomer solution;

(iii) carrying out gel-crushing of a crosslinked hydrogel polymer generated during or after the polymerization to obtain a particulate hydrogel;

(iv) drying the particulate hydrogel to obtain a dried polymer;

(v) pulverizing and/or classifying the dried polymer to obtain a particulate water-absorbing resin before surface-crosslinking;

(vi) surface-crosslinking the particulate water-absorbing resin before surface-crosslinking; and (vii) incorporating the surface-crosslinked particulate water-absorbing resin in an absorbent article, wherein in the step (i) and/or the step (ii), water-soluble polyalkylene glycol having a weight average molecular weight of not more than about 2000 is added to the aqueous monomer solution so that a total amount of the water-soluble polyalkylene glycol added in the step (i) and/or the step (ii) is about 0.01 mass % to about 1 mass % relative to a total mass of a monomer included in the aqueous monomer solution, the crosslinked hydrogel polymer has a centrifuge retention capacity of not more than about 31 g/g and not less than about 20 g/g, and the surface-crosslinked particulate poly(meth)acrylic acid (salt)-based water-absorbing resin obtained by said method satisfies (1) to (4) below:

(1) a centrifuge retention capacity (CRC) of not less than about 20 g/g and not more than about 35 g/g;

(2) an absorption against pressure (AAP), measured under a load of about 0.7 psi, of not less than about 25 g/g;

(3) a saline flow conductivity (SFC) of not less than about 15 (×about $10^{-7}$ $cm^3$·sec/g); and (4) a free swell rate (FSR) of not less than about 0.33 g/(g·s).

2. The method of claim 1, wherein the polyalkylene glycol has a weight average molecular weight of not less than about 200.

3. The method of claim 1, wherein a content of the polyalkylene glycol is adjusted to about 0.01 mass % to about 1 mass % relative to the entire surface-crosslinked particulate poly(meth)acrylic acid (salt)-based water-absorbing resin.

4. The method of claim 1, wherein the surface-crosslinked particulate poly(meth)acrylic acid (salt)-based water-absorbing resin is a surface-crosslinked water-absorbing resin having a non-uniformly pulverized shape.

5. The method of claim 1, wherein the surface-crosslinked particulate poly(meth)acrylic acid (salt)-based water-absorbing resin has a moisture content of not more than about 5 mass %.

6. The method of claim 1, wherein the particulate hydrogel obtained as a result of the gel-crushing of the crosslinked hydrogel polymer in the step (iii) has a logarithmic standard deviation (σ) of about 0.2 to about 1.5, the logarithmic standard deviation (σ) indicating a particle size distribution of the particulate hydrogel.

7. The method of claim 1, wherein the absorbent article is a paper diaper or a pant.

8. The method of claim 1, wherein, in step (vii), the surface-crosslinked particulate water-absorbing resin is incorporated into an absorbent core and the absorbent core is comprised by the absorbent article.

9. The method of claim 8, wherein the absorbent core is made by providing two nonwoven webs and incorporating the surface-crosslinked particulate water-absorbing resin between the two nonwoven webs.

10. The method of claim 9, wherein the absorbent core, in between the two nonwoven webs, comprises less than about 20 weight-% of cellulose fibers, preferably less than about 10 weight-% of cellulose fibers, and more preferably less than about 5 weight-% of cellulose fibers.

11. The method of claim 10, wherein the method comprises the further step of adhesively immobilizing the surface-crosslinked particulate water-absorbing resin in between the two nonwoven webs.

12. The method of claim 8, wherein the method comprises the further steps of:

providing a topsheet providing a backsheet providing the absorbent core in between the topsheet and the backsheet.

* * * * *